US010690611B2

(12) United States Patent
Saito et al.

(10) Patent No.: US 10,690,611 B2
(45) Date of Patent: Jun. 23, 2020

(54) SENSOR DEVICE, DETECTION METHOD, AND SENSOR UNIT

(71) Applicant: SHARP KABUSHIKI KAISHA, Sakai, Osaka (JP)

(72) Inventors: Akira Saito, Sakai (JP); Daiki Sato, Sakai (JP); Takeshi Mitsunaka, Sakai (JP); Kunihiko Iizuka, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 34 days.

(21) Appl. No.: 16/090,817

(22) PCT Filed: May 31, 2017

(86) PCT No.: PCT/JP2017/020313
§ 371 (c)(1),
(2) Date: Oct. 3, 2018

(87) PCT Pub. No.: WO2017/175879
PCT Pub. Date: Oct. 12, 2017

(65) Prior Publication Data
US 2019/0242845 A1 Aug. 8, 2019

(30) Foreign Application Priority Data

Apr. 5, 2016 (JP) .................................. 2016-076058
Jun. 30, 2016 (JP) .................................. 2016-130940

(51) Int. Cl.
*G01N 27/22* (2006.01)
*G01N 27/72* (2006.01)
(Continued)

(52) U.S. Cl.
CPC .......... *G01N 27/22* (2013.01); *G01N 15/0656* (2013.01); *G01N 15/1031* (2013.01);
(Continued)

(58) Field of Classification Search
CPC ........ G01N 27/00; G01N 27/02; G01N 27/22; G01N 27/72; G01N 15/00; G01N 15/06;
(Continued)

(56) References Cited

U.S. PATENT DOCUMENTS 6,682,649 B1    1/2004  Petersen et al.
2003/0162235 A1*  8/2003  Seino ................... G01N 27/021
                                                    435/7.23
(Continued)

FOREIGN PATENT DOCUMENTS

JP    2003-511668 A    3/2003
JP    2016-020815 A    2/2016
(Continued)

OTHER PUBLICATIONS

Jun-Chau Chien, Mekhail Anwar, Erh-Chia Yeh, Luke P. Lee, Ali M. Niknejad, "6.5/11/17.5/30-GHz high throughput interferometer-based reactance sensors using injection-locked oscillators and ping-pong nested chopping", VLSI Circuits Digest of Technical Papers, 2014 Symposium on, 1-2.

(Continued)

*Primary Examiner* — Hoai-An D. Nguyen
(74) *Attorney, Agent, or Firm* — ScienBiziP, P.C.

(57) ABSTRACT

A sensor device (30) includes an oscillation unit formed in a semiconductor integrated circuit (40) and having an oscillation frequency which changes in accordance with a physical property of an analyte which comes into contact with the oscillation unit; an oscillation frequency detection unit configured to detect the oscillation frequency, and one or more electrode pairs (36) configured to move a specific analyte dispersed in liquid to an arbitrary location.

7 Claims, 21 Drawing Sheets

(51) Int. Cl.
*G01N 33/49* (2006.01)
*G01N 33/487* (2006.01)
*G01N 33/543* (2006.01)
*G01N 15/06* (2006.01)
*G01N 15/10* (2006.01)
*G01N 15/00* (2006.01)

(52) U.S. Cl.
CPC ......... *G01N 15/1056* (2013.01); *G01N 27/72* (2013.01); *G01N 33/48707* (2013.01); *G01N 33/49* (2013.01); *G01N 33/5438* (2013.01); *G01N 2015/0053* (2013.01); *G01N 2015/1006* (2013.01)

(58) Field of Classification Search
CPC ............... G01N 15/0656; G01N 15/10; G01N 15/1031; G01N 15/1056; G01N 2015/0042; G01N 2015/0053; G01N 33/00; G01N 33/48; G01N 33/483; G01N 33/487; G01N 33/48707; G01N 33/49; G01N 33/50; G01N 33/53; G01N 33/543; G01N 33/54366; G01N 33/54373; G01N 33/5438
USPC ....... 324/600, 649, 658, 663, 681, 682, 691, 324/713, 715, 717, 719; 204/193, 194, 204/196.01, 196.06, 229.8, 400, 403.01, 204/554, 556; 205/80, 81, 334, 335, 640, 205/645, 775, 776.5, 777.5; 435/4, 9, 29, 435/31, 32, 34, 283.1, 287.1, 287.3, 435/287.4, 287.7; 422/50, 68.1, 82.01, 422/83, 98
See application file for complete search history.

(56) References Cited

U.S. PATENT DOCUMENTS

2004/0055901 A1    3/2004  Petersen et al.
2006/0014270 A1*   1/2006  Mansson .................. G01N 5/02
                                                    435/287.2
2008/0160600 A1*   7/2008  Zuccato ........... G01N 33/54373
                                                    435/287.2
2013/0337498 A1   12/2013  Tokonami et al.
2015/0109004 A1    4/2015  Blaschke et al.

FOREIGN PATENT DOCUMENTS

WO    2012-121229 A1    9/2012
WO    2017-010177 A1    1/2017

OTHER PUBLICATIONS

Jun-Chau Chien, Mekhail Anwar, Erh-Chia Yeh, Luke P. Lee, Ali M. Niknejad, "A 6.5/17.5-GHz dual-channel interferometer-based capacitive Sensor in 65-nm CMOS for high-speed flow cytometry", Microwave Symposium (IMS), 2014IEEE MTT-S International, 1-4.

Yuhki Yanase, Takaaki Hiragun, Tetsuji Yanase, Tomoko Kawaguchi, Kaori Ishii, Michihiro Hide, "Evaluation of peripheral blood basophil activation by means of surface plasmon resonance imaging", Biosensors and Bioelectronics 32 (2012) 62-68.

* cited by examiner

FIG. 15
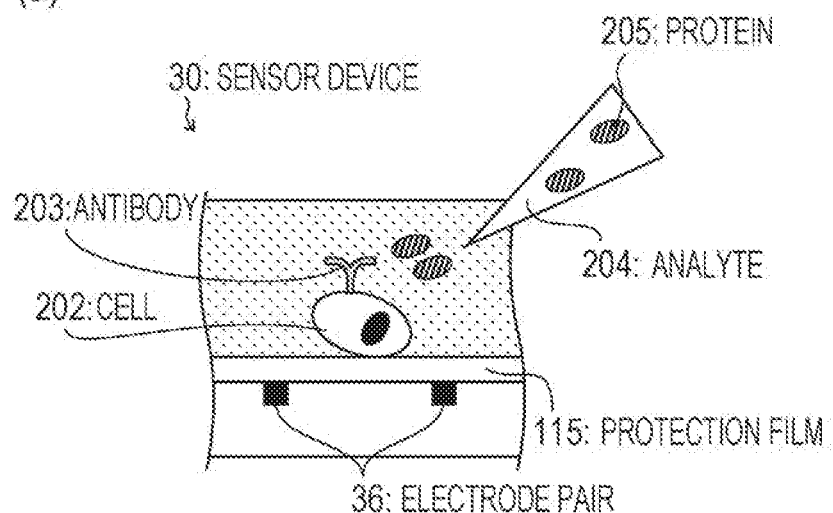
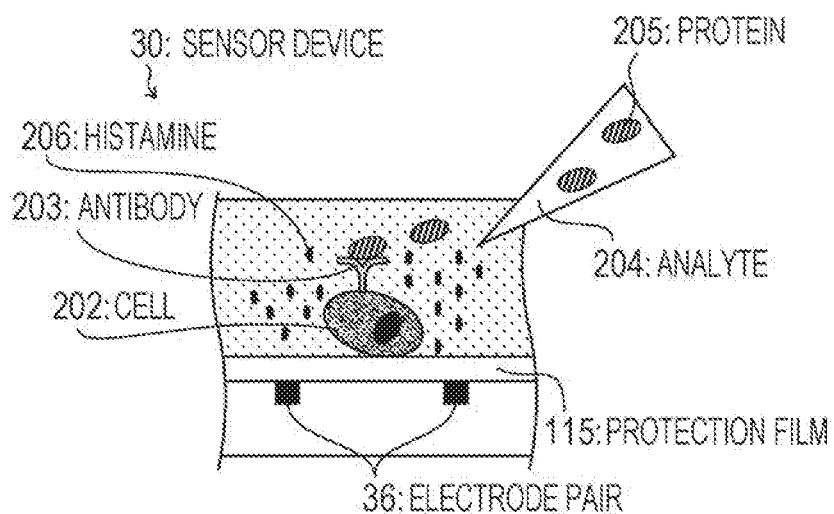

FIG. 16
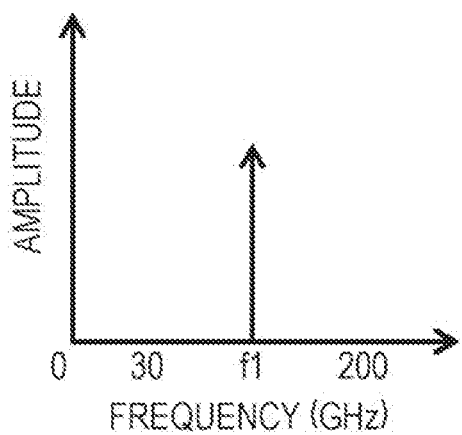
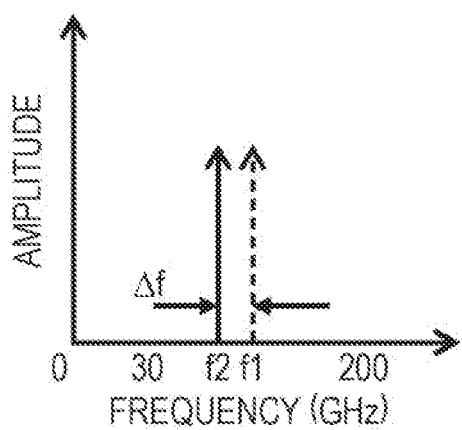

SENSOR DEVICE, DETECTION METHOD, AND SENSOR UNIT

TECHNICAL FIELD

The present invention relates to sensor devices, detection methods, and sensor units and, more specifically, to a sensor device, a detection method, and a sensor unit which detect an analyte existing in liquid and a state of the analyte.

BACKGROUND ART

A diagnostic apparatus for human body for use in each home, clinic, and the like requires a reduced price, a reduced size, a shortened test time, convenience of operation, and the like. Examples of a diagnostic apparatus which satisfies such requirements include a sensor device formed in a semiconductor integrated circuit (for example, NPL 1 and NPL 2).

FIG. 20 shows a conventional sensor device disclosed in NPL 1 and NPL 2. As shown in FIG. 20, a sensor device 10 is formed in a semiconductor integrated circuit and includes an oscillation unit 11 and an oscillation frequency detection unit 12. The oscillation unit 11 includes a resistor R1 and a resonator 13. The resonator 13 includes cross-coupled transistors M1 and M2, inductors L1 and L2, two sensing electrodes 14 to be brought into contact with an analyte 20, and a capacitor C3. The resonance frequency of the resonator 13 is 6 GHz to 30 GHz.

FIG. 21 shows a perspective view illustrating the two sensing electrodes 14. Moreover, FIG. 22 shows a sectional view illustrating plate-shaped electrodes 141 and 142 and peripheral members taken along line A-A in the arrow direction of FIG. 21. As illustrated in FIG. 21, each sensing electrode 14 includes the two plate-shaped electrodes 141 and 142 each having a rectangular parallelepiped shape.

As illustrated in FIG. 22, the plate-shaped electrodes 141 and 142 are formed in a metal wiring layer which is the uppermost layer of a semiconductor integrated circuit. Moreover, an interlayer insulating film 16 is disposed between metal wiring layers of the semiconductor integrated circuit. In FIG. 22, only the uppermost metal wiring layer and the interlayer insulating film 16 under the uppermost metal wiring layer are shown for the sake of convenience. The interlayer insulating film 16 has a surface covered with a surface protection film 15, and the surface protection film 15 has openings in regions where the two plate-shaped electrodes 141 and 142 are disposed. Thus, exposed upper surfaces of the late-shaped electrodes 141 and 142 directly come into contact with the analyte 20.

Next, operation of the sensor device 10 will be described. When the permittivity of the analyte 20 located in the vicinity of the sensing electrodes 14 changes, a parasitic capacitance value with respect to the sensing electrodes 14 changes, and the resonance frequency of the resonator 13 changes. A change of the oscillation frequency of the oscillation unit 11 alone with the change of the resonance frequency is detected by the oscillation frequency detection unit 12. The above-described operation enables the sensor device 10 to detect the change of the permittivity occurred in the analyte 20 located in the vicinity of the sensing electrodes 14 as the change of the oscillation frequency of the oscillation unit 11.

CITATION LIST

Non Patent Literature

NPL 1: Jun-Chau Chien, Mekhail Anwar, Erh-Chia Yeh, Luke P. Lee, Ali M. Niknejad, "6.5/11/17.5/30-GHz high throughput interferometer-based reactance sensors using injection-locked oscillators and ping-pong nested chopping", VLSI Circuits Digest of Technical Papers, 2014 Symposium on, 1-2

NPL 2: Jun-Chau Chien, Mekhail Anwar, Erh-Chia Yeh, Luke P. Lee, Aid M. Niknejad, "A. 6.5/17.5-GHz dual-channel interferometer-based capacitive Sensor in 65-nm CMOS for high-speed flow cytometry", Microwave Symposium (IMS), 2014IEEE MTT-S International, 1-4

NPL 3: Yuhki Yanase, Takaaki Hiragun, Tetsuji Yanase, Tomoko Kawaguchi, Kaori Ishii, Mdchihiro Hide, "Evaluation of peripheral blood basophil activation by means of surface plasmon resonance imaging", Biosensors and Bioelectronics 32 (2012) 62-68

SUMMARY OF INVENTION

Technical Problem

It is known that in order to detect a change of the permittivity of the analyte 20 located in the vicinity of the sensing electrodes 14 as a change of the oscillation frequency of the oscillation unit 11 along with a change of a parasitic capacitance value with respect to the sensing electrodes 14 so as to detect the analyte 20, the sensor device 10 shown in FIG. 20 has such a sensitivity distribution that on a sensor surface, sensitivity to the analyte 20 is maximum in the vicinity of the sensing electrodes 14.

Dielectric particles, such as cells, as examples of the analyte are, in many cases, tested in liquid. Thus, when the semiconductor integrated circuit in which the sensor device of FIG. 20 is formed is used alone, and sensing is attempted by bringing liquid containing analytes into contact with the sensor device, detection sensitivity to analytes as targets is low because no means which selectively arranges the analytes as targets in an appropriate position on the sensor surface is provided. Moreover, the detection sensitivity depends on the distribution of the analytes as targets in the liquid.

In the sensor device disclosed in NPL 1 and NPL 2, in order to arrange analytes in the vicinity of the sensing electrodes, a micro flow path is integrated with the semiconductor integrated circuit in which the sensor device is formed. The micro flow path is made of SU-8 which is a photoresist and polydimethylsiloxane (PDMS) which is a kind of silicone rubber. In this way, flow of the liquid is controlled to solve the problems.

Integrating the micro flow path with the semiconductor integrated circuit, however, involves problems that a process required in addition to a semiconductor process complicates a series of production processes and that a pump (for example, a syringe pump) serving as drive force of the liquid has to be disposed outside, and a device after the integration of the micro flow path has thus an increased size.

Thus, in view of the foregoing, an object of the present invention is to provide a sensor device, a detection method, and a sensor unit which easily enable detection sensitivity to an analyte as a target dispersed in liquid to be increased.

Solution to Problem

To solve the problems, a sensor device according to one aspect of the present invention includes: an oscillation unit formed in a semiconductor integrated circuit and having an oscillation frequency which changes in accordance with a physical property of an analyte which comes into contact with the oscillation unit; an oscillation frequency detection unit configured to detect the oscillation frequency; and at least one electrode pair configured to move a specific analyte dispersed in liquid to an arbitrary location.

Advantageous Effects of Invention

One aspect of the present invention easily improves the detection sensitivity to an analyte as a target dispersed in liquid.

BRIEF DESCRIPTION OF DRAWINGS

FIG. 15 is a sectional view taken along line A-A' in the arrow direction of FIG. 10(a).

FIG. 16 is a view illustrating an oscillation frequency of as oscillation unit, the oscillation frequency being detected by an oscillation frequency detection unit.

DESCRIPTION OF EMBODIMENTS

Figure 1:
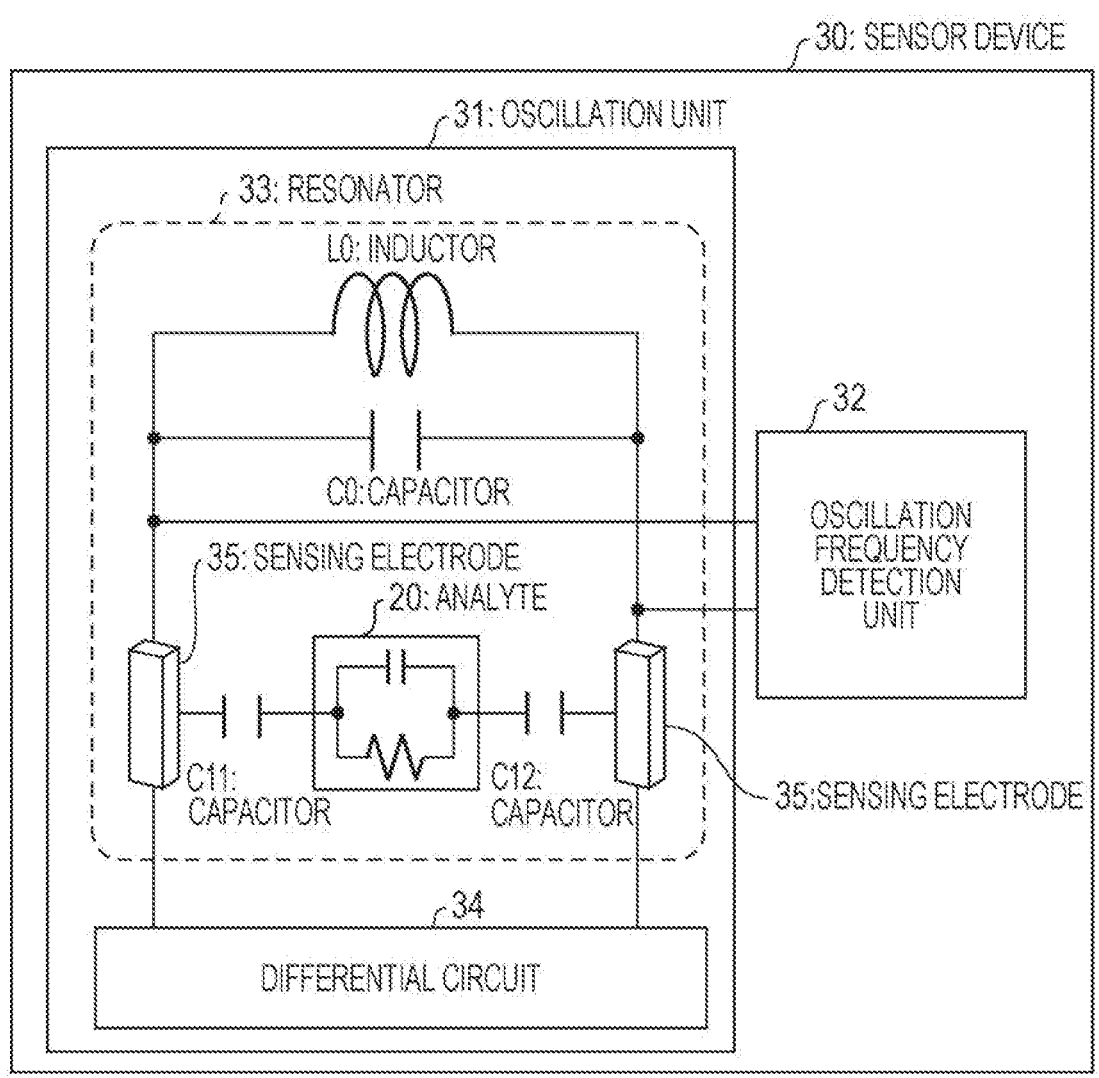
FIG. 1 is a block diagram illustrating a configuration of a sensor device according to an embodiment of the present invention.

Embodiments of the present invention will be described in detail below. Note that configurations described in the following embodiments are not to limit the scope of the present invention to the illustrated configurations and are merely illustrative examples, unless otherwise specified. Note that components having the same function are denoted by the same reference numerals in the drawings described below, and the repetitive description thereof is omitted.

[Description of Basic Sensor Device]

The configuration and operation of a sensor device commonly used in the embodiments described below will be described. The sensor device is configured to sense the permittivity or the magnetic permeability of an analyte by bringing the analyte into contact with a surface of a semiconductor integrated circuit, or a physical property such as a permittivity or a magnetic permeability which changes when the property of the analyte changes.

(Configuration of Sensor Device)

FIG. 1 is a block diagram illustrating a configuration of a sensor device 30 of each of the embodiments. As shown in FIG. 1, the sensor device 30 includes an oscillation unit 31 and an oscillation frequency detection unit 32.

The oscillation unit 31 is an LC oscillation circuit including a resonator 33, a differential circuit 34, and sensing electrodes 35 and is formed as a part of a semiconductor integrated circuit on a semiconductor integrated circuit substrate which is not shown. The oscillation unit 31 has an oscillation frequency which changes in accordance with the physical property of an analyte 20 which comes into contact with the oscillation unit 31. The sensor device 30 will be described below with reference to an example in which the oscillation frequency changes in accordance with the complex permittivity of the analyte 20 which comes into contact with the sensor device 30.

A main analyte 20 of the sensor device 30 is a biological cell or a tissue containing water as a main component. In a frequency from 30 GHz to 200 GHz, a change of the complex permittivity of water is large, and a change of the frequency characteristic of the permittivity can be detected with high sensitivity. Therefore, the oscillation frequency of the oscillation unit 31 is preferably 30 GHz to 200 GHz.

The resonator 33 includes capacitors $C0$, $C11$, $C12$, and an inductor $L0$. The inductor $L0$ and the capacitor $C0$ are connected in parallel to each other. The capacitor $C11$ has one end connected to one of a pair of plate-shaped electrodes constituting the sensing electrodes 35. The capacitor $C12$ has one end connected to the other of the pair of plate-shaped electrodes constituting the sensing electrodes 35.

The analyte 20 is in contact with the other end of the capacitor C11 and the other end of the C12. Thus, the capacitors C11 and C12 are connected to the analyte 20 in series. The capacitors C11 and C12 include a protection film on a surface of the semiconductor integrated circuit substrate which is not shown.

Moreover, the resonator 33 has a resonance frequency which changes in accordance with the complex permittivity of the analyte 20. The resonator 33 serves as a sensor unit configured to detect a complex permittivity. The capacitor C0 may be made of parasitic capacitance of a wire or a differential circuit 6 which not shown.

The oscillation frequency detection unit 32 is a unit configured to detect the oscillation frequency of the oscillation unit 31. As the oscillation frequency detection unit 32, a known frequency detection circuit may be used. The oscillation frequency detection unit 32 may be formed in the semiconductor integrated circuit or be formed outside the semiconductor integrated circuit.

The differential circuit 34 is a circuit including a differential transistor pair and is accordingly formed of, for example, a known differential circuit such as a differential circuit including a plurality of transistors cross-coupled to each other.

Here, the sensor device 30 includes a means which moves the analyte 20. Specifically, the sensor device 30 includes an electrode pair as the means which move the analyte 20. This will be described later.

(Oscillation Frequency of Oscillation Unit)

Figure 2:
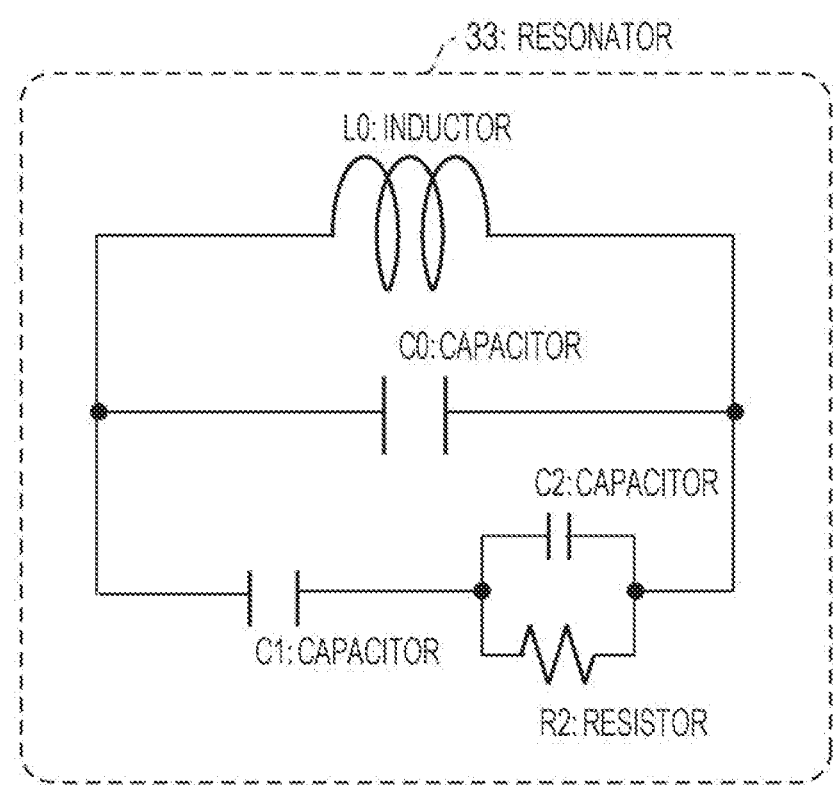
FIG. 2 is a circuit diagram illustrating an equivalent circuit of a resonator according to the embodiment of the present invention.

Next, the relationship between the complex permittivity of the analyte 20 and the oscillation frequency of the oscillation unit will be described. FIG. 2 is a circuit diagram illustrating an equivalent circuit of the resonator 33.

The following, formula (1) is obtained, where the capacitance detected in a case of the analyte 20 being air is denoted by Cair, and the relative complex permittivity of the analyte 20 is expressed as: $\varepsilon = \varepsilon_r - j\varepsilon_i$.

[Math. 1]

$$G_2 + j\omega C_2 = j\omega C_{air}\varepsilon \qquad (1)$$
$$= j\omega C_{air}(\varepsilon_r - j\varepsilon_i)$$
$$= j\omega C_{air}\varepsilon_i + j\omega C_{air}\varepsilon_r$$

In the formula (1), C2 and G2 (=1/R2(resistor)) are respectively capacitance and conductance which the analyte 20 has, and the resonator 33 is expressed as an equivalent circuit shown in FIG. 2.

In FIG. 2, the capacitors C11 and C12 are collectively expressed as a single capacitor C1 for simplicity of calculation. In consideration of resonance conditions, the oscillation frequency fres of the oscillation unit 31 can be expressed as the following formula (2).

[Math. 2]

$$f_{res} = \frac{1}{2\pi\sqrt{L_0\left(C_0 + C_1 C_{air} \frac{\varepsilon_r C_1 + (\varepsilon_r^2 + \varepsilon_i^2)C_{air}}{(C_1 + \varepsilon_r C_{air})^2 + (\varepsilon_i C_{air})^2}\right)}} \qquad (2)$$

Thus, it can be seen that the oscillation frequency fres is a function of both the real part and the imaginary part of the complex permittivity.

(Operation of Sensor Device)

Next, operation of the sensor device 30 will be described.

The sensor device 30 detects the complex permittivity of the analyte 20 as the resonance frequency of the resonator 33. The analyte 20 is connected in series between two electrodes constituting the sensing electrodes 35 included in the resonator 33 via the capacitor C11 and the capacitor C12. The oscillation frequency detection unit 12 detects the oscillation frequency of the oscillation unit 31 as the resonance frequency of the resonator 33. That is, in the sensor device 30, the oscillation frequency detection unit 12 detects the complex permittivity of the analyte 20 as the oscillation frequency of the oscillation unit 31.

When the complex permittivity of the analyte 20 changes, the resonance frequency of the resonator 33 changes. The oscillation frequency detection unit 32 detects the change of the oscillation frequency of the oscillation unit 31 along with the change of the resonance frequency. Thus, in the sensor device 30, the oscillation frequency detection unit 12 detects the change of the complex permittivity of the analyte 20 as the change of the oscillation frequency of the oscillation unit 31.

(Analyte Moving Means)

Figure 3:
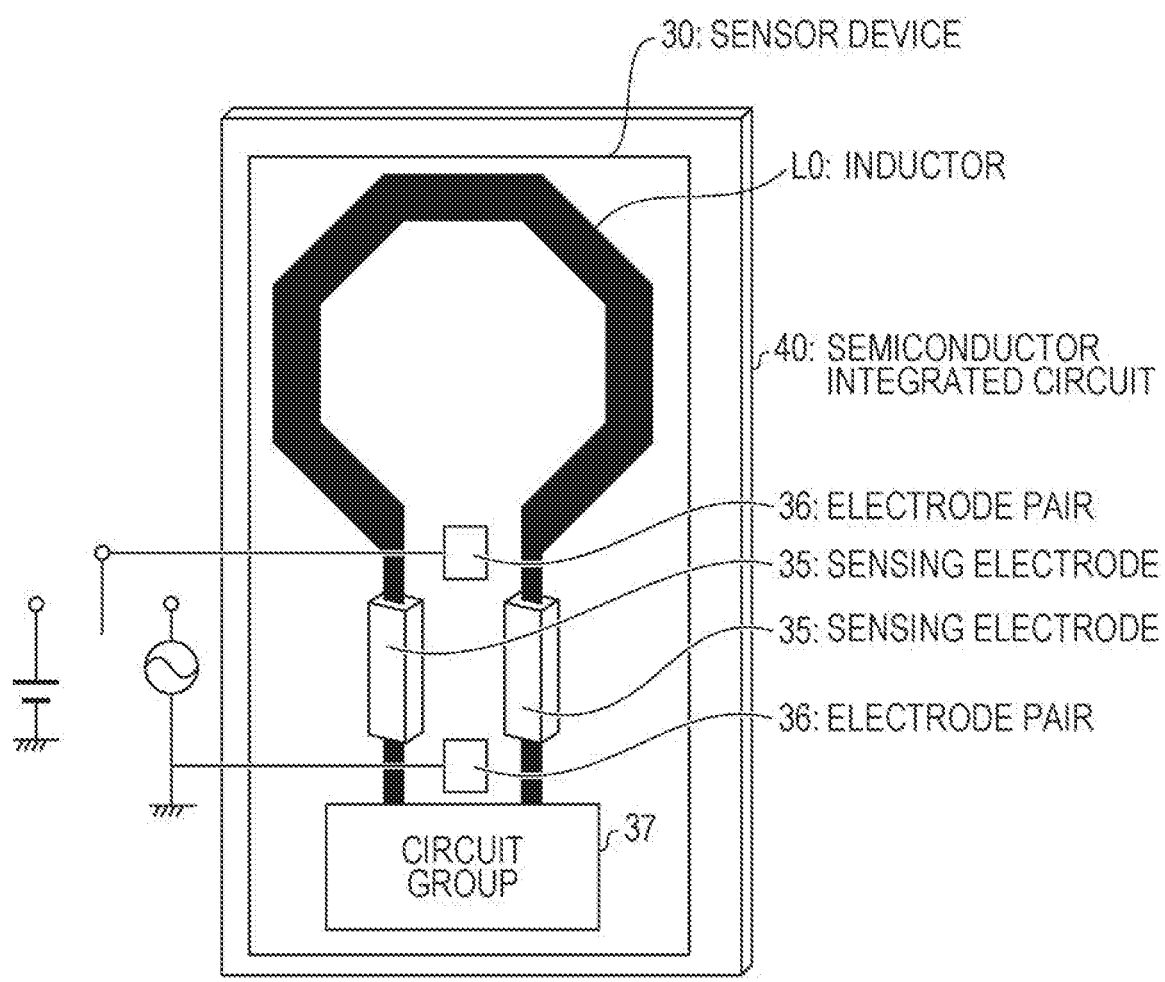
FIG. 3 is a view schematically illustrating a semiconductor integrated circuit in which the sensor device according to the embodiment of the present invention is formed, the sensor device including an electrode pair as an analyte moving means.

The analyte moving means of the sensor device 30 will be described below. FIG. 3 is a view schematically illustrating a semiconductor integrated circuit 40 in which the sensor device 30 is formed, the sensor device including an electrode pair 36 as the analyte moving means.

As shown in FIG. 3, the sensor device 30 of FIG. 1 is formed in the semiconductor integrated circuit 40. In FIG. 3, the capacitors C0, C11, C12, the oscillation frequency detection unit 32, and the differential circuit 34 of FIG. 1 are are collectively shown as a circuit group 37.

A metal layer of a semiconductor integrated circuit in which the sensor device 30 is configured forms the electrode pair 36 including one or more pairs of electrodes in the vicinity of the sensing electrodes 35. An alternating-current voltage signal or a direct-current voltage signal is applicable to the electrode pair 36 from the outside of the sensor device 30, and an electric field generated by the voltage signal enables an analyte in the vicinity of the electrode pair 36 to be moved.

Thus, dielectrophoretic force or electrophoresis force generated by applying the voltage signal to the electrode pair 36 can be used to move the analyte to an arbitrary location. For example, the voltage signal is applied to the electrode pair 36 to move the analyte to the vicinity of the sensing electrodes 35 of the oscillation unit 31, which enables the detection sensitivity of the sensor device 30 to the analyte to be improved. When the sensor device 30 is used, the detection sensitivity to the analyte as a target dispersed in liquid can be easily improved simply by using the electrode pair 36.

In order to improve the efficiency of force that moves the analyte with respect to the magnitude of the effective value of an applied voltage, an electric field in the vicinity of the electrode pair 36 is preferably reinforced by forming the electrode pair 36 from a metal layer in the vicinity of the surface layer of the semiconductor integrated circuit, in particular, a top metal layer. This increases the electric field strength generated by the voltage signal applied to the electrode pair 36 in the vicinity of the surface of the sensor device 30, thereby providing the effect of increasing the dielectrophoretic force with respect to the analyte. Moreover, in order to improve the sensitivity to the complex permittivity of the analyte, the sensing electrodes 35 are preferably formed from a metal layer in the vicinity of the surface layer of the semiconductor integrated circuit, in particular, a top metal layer. This increases the electric field strength generated by the sensing electrodes 35 in the vicinity of the surface of the sensor device 30, thereby providing the effect of increasing the sensitivity of the sensor device 30 to the complex permittivity of the analyte. Moreover, since the electrode pair 36 and the sensing electrodes 35 are integrated into the semiconductor integrated circuit 40, the sensor device 30 can be downsized.

The oscillation frequency detection unit 12 of the sensor device 30 detects the complex permittivity of the analyte as the resonance frequency of the resonator 33 of FIG. 1, the analyte being connected in series between two electrodes constituting the sensing electrodes 35 included in the resonator 33 via the capacitor C11 and the capacitor C12. This is equivalent to detecting the complex permittivity of the analyte present in the vicinity of the sensing electrodes 35 in FIG. 3.

Influence over a detection frequency is mainly caused due to the presence of the analyte present in an intermediate region (intermediate location) between two plate-shaped electrodes constituting the sensing electrodes 35. Thus, a location at which the effective value of the electric field strength generated due to the voltage signal applied to the electrode pair 36 is largest, that is, an intermediate region between the electrode pair 36 is accordingly designed to overlap the intermediate region between the two plate-shaped electrodes constituting the sensing electrodes 35. Thus, it is possible to move the analyte to the intermediate region between the two plate-shaped electrodes constituting the sensing electrodes 35.

First Embodiment (Configuration of Sensor Device)

The configuration of a sensor device according to the present embodiment is similar to that of the sensor device 30 shown in FIG. 3.

(Operation and Effect)

Figure 4:
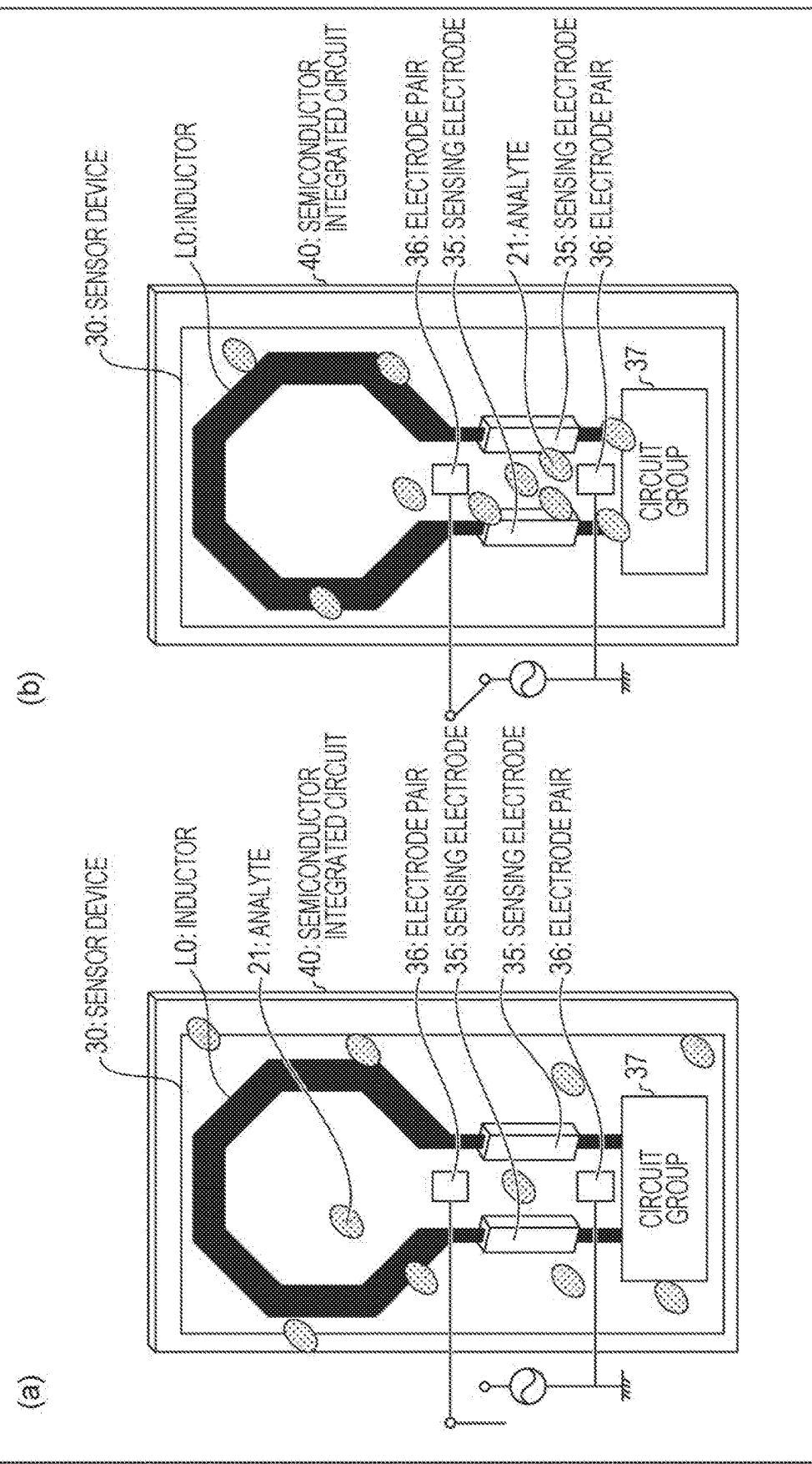
FIG. 4(a) is a view illustrating a state before an alternating-current voltage signal is applied to an electrode pair.
FIG. 4(b) is a view illustrating a state after the alternating-current voltage signal is applied to the electrode pair.

An example in which a sensor device 30 according to the present embodiment is used in liquid containing one kind of analyte dispersed therein will be described with reference to FIG. 4. FIG. 4(a) is a view illustrating a state before an alternating-current voltage signal is applied to an electrode pair 36, and FIG. 4(b) is a view illustrating a state after the alternating-current voltage signal is applied to the electrode pair 36.

First, as illustrated in FIG. 4(a), liquid (not shown here) containing one kind of analyte 21, dielectric particles such as cells, is brought into contact with a surface of the sensor device 30. Here, the kind of liquid is arbitrarily selectable. For example, when cells are adopted as the analyte 21, phosphate-buffered saline (PBS) is generally used as the liquid in order to maintain an appropriate value of pH or osmotic pressure in the periphery of the cells.

Next, an alternating-current voltage signal having an angular frequency ω is applied to the electrode pair 36. Dielectrophoretic force <FDEP> applied to the analyte 21 in the liquid by a sine wave voltage signal having an angular frequency ω is expressed as the following formula (3), where the liquid has a complex permittivity εm*=εm−jσm/ω, the analyte has a complex permittivity εp*=εp−jσp/ω, the analyte has a radius r, and the electric field strength generated by a sine wave voltage has an effective value ERMS.

[Math. 3]

$$\langle \vec{F}_{DEP} \rangle = \pi \varepsilon_m r^3 \mathrm{Re}\left[\frac{\varepsilon_p^* - \varepsilon_m^*}{\varepsilon_p^* + 2\varepsilon_m^*}\right] \nabla |\vec{E}_{RMS}|^2 \quad (3)$$

When Re[(εp*−εm*)/(εp*2εem*)] in formula (3) is positive, force (positive dielectrophoretic force) in a direction in which the electric field strength is high is applied to the analyte 21. When Re[(εp*−εm*)/(εp*2εm*)] in formula (3) is negative, force (negative dielectrophoretic force) is applied against the force in the direction in which the electric field strength is high.

In the present embodiment, the angular frequency ω of the alternating-current voltage signal is selected so that the analyte 21 receives force in the direction in which the electric field strength is high, that is, toward the intermediate region between the electrode pair 36 to which the alternating-current voltage signal is applied. The alternating-current voltage signal is not limited to the sine wave as long as it corresponds to a periodical function.

In a case of analytes such as cells, the frequency f(=ω/2π) of the alternating-current voltage signal applied to the electrode pair 36 is in many cases selected from several kHz to several hundred MHz. The frequency is deviated from the oscillation frequency (30 GHz to 200 GHz) which the oscillation frequency detection unit 12 of the present embodiment detects. Therefore, detection performed by the oscillation frequency detection unit 12 is not inhibited even when a test is conducted while the alternating-current voltage signal is applied to the electrode pair 36.

As illustrated in FIG. 4(b), pieces of the analyte 21 are collected in an intermediate region between the electrode pair 36 due to positive dielectrophoretic force. The intermediate region is designed to overlap an intermediate region between two plate-shaped electrodes constituting sensing electrodes 35. Thus, the oscillation frequency detection unit 12 in this state detects the oscillation frequency of the oscillation unit 31, and thereby, the oscillation frequency as the complex permittivity of the analyte 21 and a change of the oscillation frequency along with a change of the complex permittivity of the analyte 21 can be detected with high sensitivity.

For example, it is known that the dielectric property of a normal cell and the dielectric property of a cancer cell are different from each other. Cells suspected to be cancerous and cells guaranteed to be normal are cultured, and liquid media containing the cultured cells are tested by using the sensor device 30 according to the present embodiment. By using the sensor device 30, the oscillation frequencies of the oscillation unit 31 for both the cells are obtained, and the oscillation frequencies for both the cells are compared with each other. In this way, it becomes possible to determine whether the cells suspected to be cancerous are cancerous or normal.

Second Embodiment (Configuration of Sensor Device)

The configuration of a sensor device according to the present embodiment is similar to that of the sensor device 30 shown in FIG. 3.

(Operation and Effect)

Figure 5:
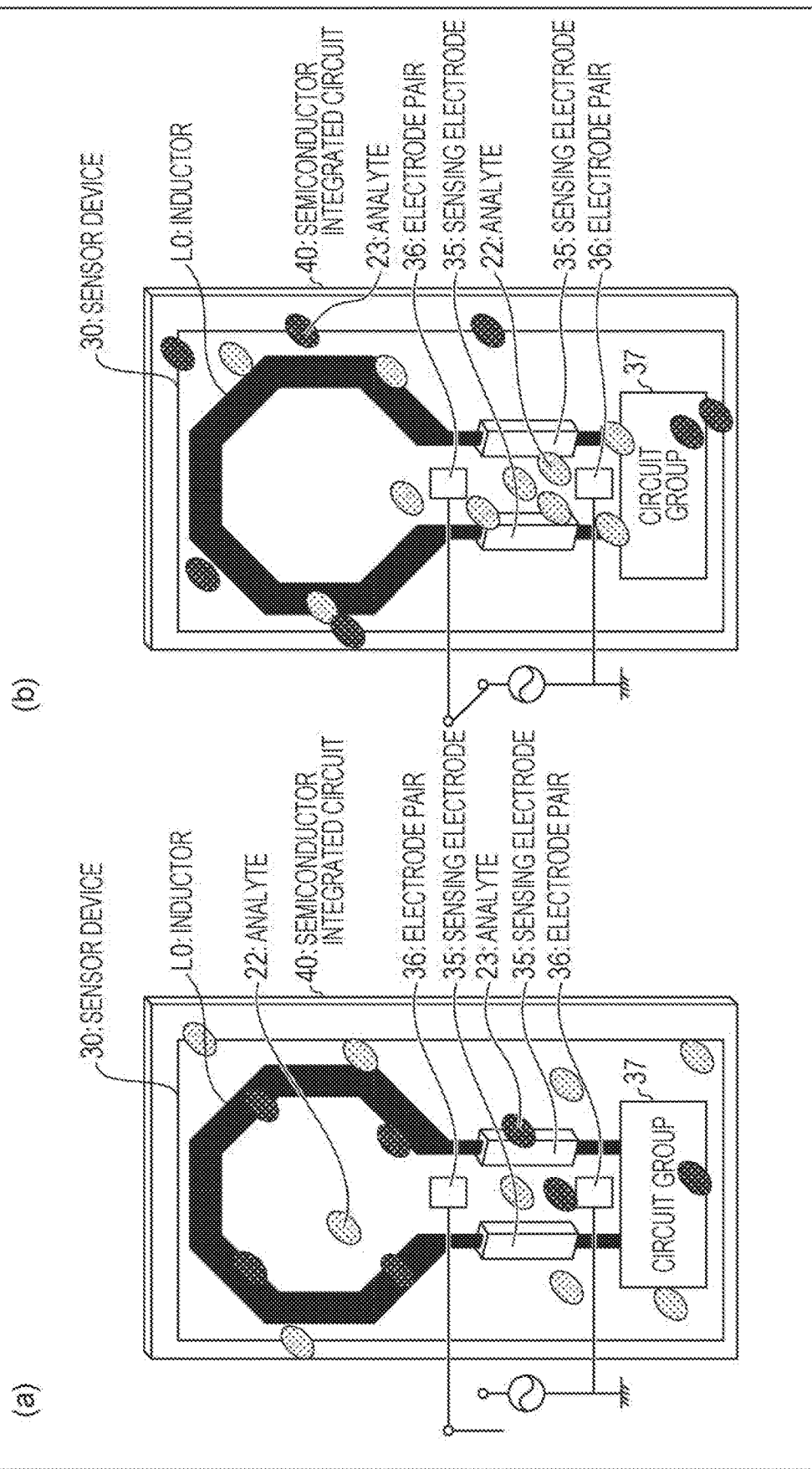
FIG. 5(a) is a view illustrating a state before an alternating-current voltage signal is applied to an electrode pair.
FIG. 5(b) is a view illustrating a state after the alternating-current voltage signal is applied to the electrode pair.

An example in which a sensor device 30 according to the present embodiment is used in liquid containing two or more kinds of dielectric particles dispersed therein will be described with reference to FIG. 5. FIG. 5(a) is a view illustrating a state before an alternating-current voltage signal is applied to an electrode pair 36, and FIG. 5(b) is a view illustrating a state after the alternating-current voltage signal is applied to the electrode par 36.

First, as illustrated in FIG. 5(a), liquid (not shown here) containing two or more kinds of analytes, dielectric particles such as cells, is brought into contact with a surface of the sensor device 30. In the figure, two kinds of analytes, an analyte 22 which is a target and an analyte 23 which is not a target, are dispersed in the liquid. Note that a plurality of kinds of analytes 23 which are not targets may be dispersed.

Next, an alternating-current voltage signal having an angular frequency ω is applied to the electrode pair 36. In the present embodiment, the angular frequency ω of the alternating-current voltage signal is selected such that positive dielectrophoretic force is applied to the analyte 22, which is a target, and negative dielectrophoretic force is applied to the analyte 23, which is not a target.

As illustrated in FIG. 4(b), the dielectrophoretic force generated by the alternating-current voltage signal causes pieces of the analyte 22, which is a target, to be collected in an intermediate region between the electrode pair 36, that is, an intermediate region between the sensing electrodes 35, and the analyte 23, which is not a target, to go away from the sensing electrodes 35. The oscillation frequency detection unit 12 in this state detects the oscillation frequency of the oscillation unit 31, and thereby, the oscillation frequency as the complex permittivity of the analyte 22, which is a target, and a change of the oscillation frequency along with a change of the complex permittivity of the analyte 22 can be selectively detected even in liquid containing the analyte 23 other than the analyte 22, which is a target.

For example, blood is liquid as blood plasma in which a plurality of types of blood cells such as erythrocytes are dispersed. The angular frequency ω of the alternating-current voltage signal is appropriately configured in accordance with the dielectric property of blood cells which are targets in the blood, and then, the blood is, tested by using the sensor device 30 according to the present embodiment. In this way, the dielectric property with respect to the blood cells which are the targets can be measured simply by the sensor device 30 according to the present embodiment without performing a component separation process such as centrifugal separation of the blood.

Third Embodiment (Configuration of Sensor Unit)

Figure 6:
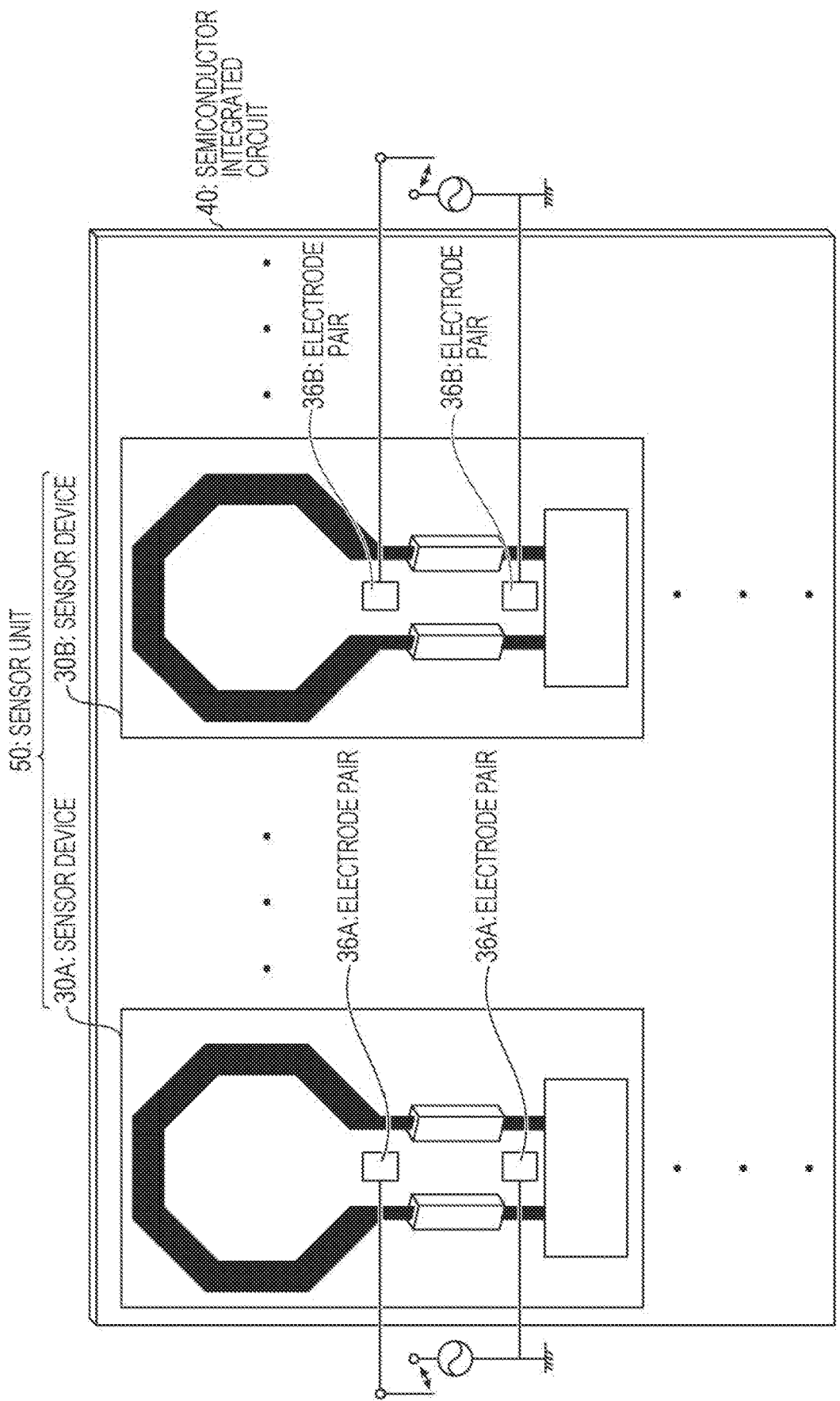
FIG. 6 is a view schematically illustrating a semiconductor integrated circuit in which a sensor unit according to an embodiment of the present invention is formed.

With reference to FIG. 6, the configuration of the sensor unit according to the present embodiment will be described. FIG. 6 is a view schematically illustrating a semiconductor integrated circuit 40 in which a sensor unit 50 is formed.

As illustrated in FIG. 6, the sensor unit 50 is formed in the semiconductor integrated circuit 40, and the sensor unit 50 includes a plurality of sensor devices 30A, 30E, . . . . The configuration of each of the sensor devices 30A, 30B, . . . is similar to that of the sensor device 30 shown in FIG. 3. The sensor devices 30A, 30B, . . . may individually include or snare electrode pairs 6A, 36B, . . . .

(Operation and Effect)

Figure 7:
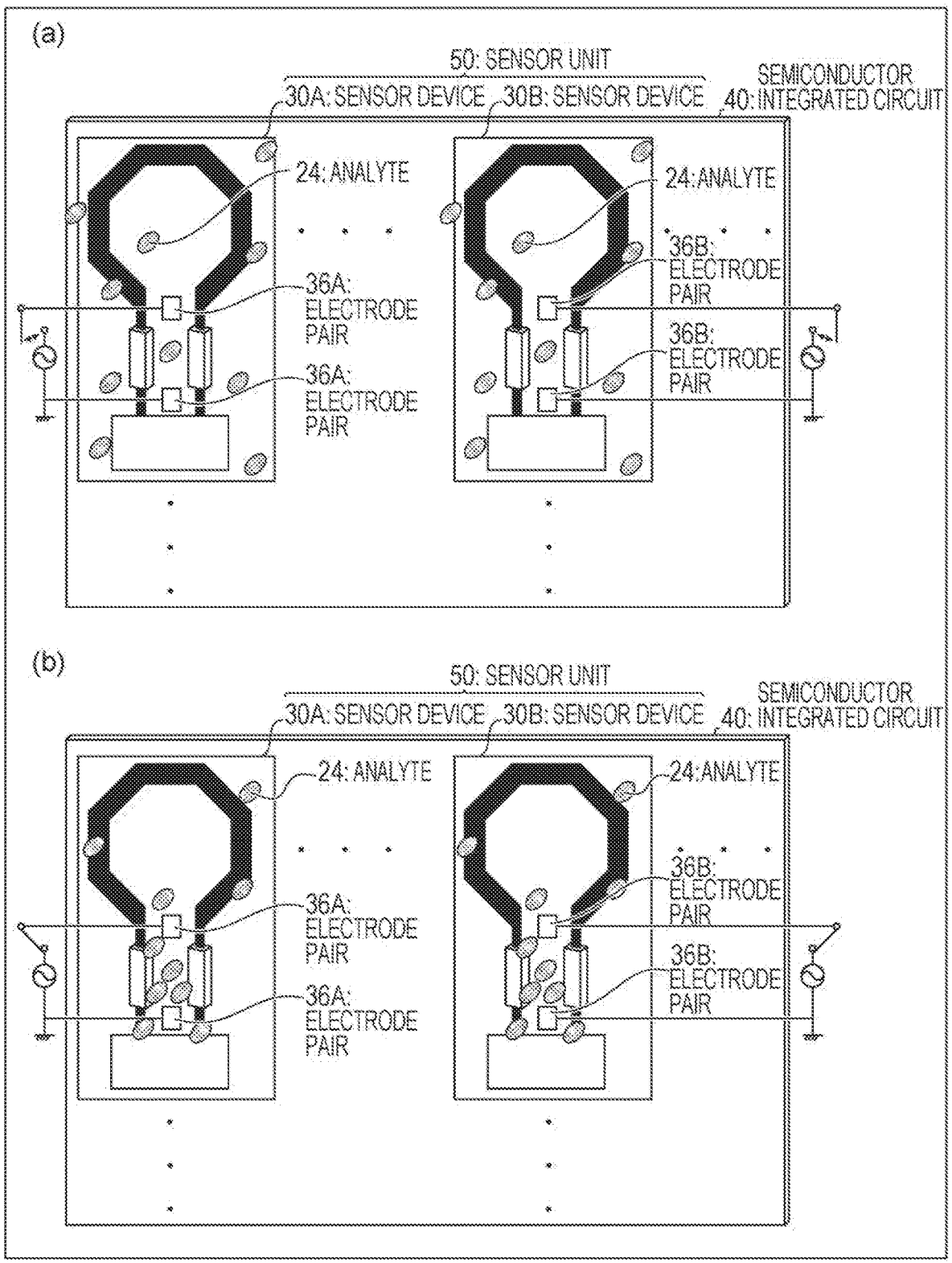
FIG. 7(a) is a view illustrating a state before an alternating-current voltage signal is applied to an electrode pair.
FIG. 7(b) is a view illustrating a state after the alternating-current voltage signal is applied to the electrode pair.

An example in which the sensor unit 50 according to the present embodiment is used in liquid containing one kind of analyte dispersed therein will be described with reference to FIG. 7. FIG. 7(a) is a view illustrating a state before an alternating-current voltage signal is applied to the electrode pairs 36A, 36B, . . . , and FIG. 7(b) is a view illustrating a state after the alternating-current voltage signal is applied to the electrode pairs 36A, 36B, . . . .

First, as illustrated in FIG. 7(a), liquid (not shown here) containing one kind of analyte 24, dielectric particles such as cells, is brought into contact with a surface of each of the sensor devices 30A, 30B, . . . . Note that the liquid may contain an analyte which is not a target as described in the second embodiment.

Next, the alternating-current voltage signal having an angular frequency ω is applied to the electrode pairs 36A, 36B, . . . . In the present embodiment, the angular frequency ω of the alternating-current voltage signal is selected so that positive dielectrophoretic force is applied to the analyte 24.

As illustrated in FIG. 7(b), the dielectrophoretic force generated by the alternating-current voltage signal causes pieces of the analyte 24 to be collected in an intermediate region between the electrode pairs 36A, 36B, . . . , that is, an intermediate region between the sensing electrodes 35 of each of the sensor devices 30A, 30B, . . . . The analyte 24 contained in the liquid has a concentration distribution on surfaces of the sensor devices 30A, 30B, . . . , and the number of the pieces of the analyte 24 collected in the intermediate region between the sensing electrodes 35 of each of the sensor devices 30A, 30B, . . . due to the positive dielectrophoretic force is influenced by the concentration of the analyte 24 in the vicinity of the electrode pairs 36A, 36B, . . . .

Thus, in the sensor unit 50 according to the present embodiment, an oscillation frequency detection unit 12 of each of the sensor devices 30A, 30B, . . . detects and compares the oscillation frequencies of the oscillation units 31 with each other, and thus, it becomes possible to reduce the influence of the concentration distribution of the analyte 24 on the surface of each of the sensor devices 30A, 30B, . . . over the detection sensitivity of each of the sensor devices 30A, 30B, . . . .

Note that when the liquid contains an analyte which is not a target, an operation similar to that of the second embodiment is performed. Thus, the oscillation frequency detection unit 12 of each of the sensor devices 30A, 30B, . . . can detect the oscillation frequency of the oscillation unit 31 with only pieces of the analyte, which is a target, being collected in the intermediate region between the sensing electrodes 35 of each of the sensor devices 30A, 30B, . . . .

Fourth Embodiment (Configuration of Sensor Unit)

A sensor unit according to the present embodiment has a configuration similar to that of the sensor unit 50 shown in FIG. 6. Note that sensor devices 30A, 30B, . . . individually include electrode pairs 36A, 36B, . . . .

(Operation and Effect)

Figure 8:
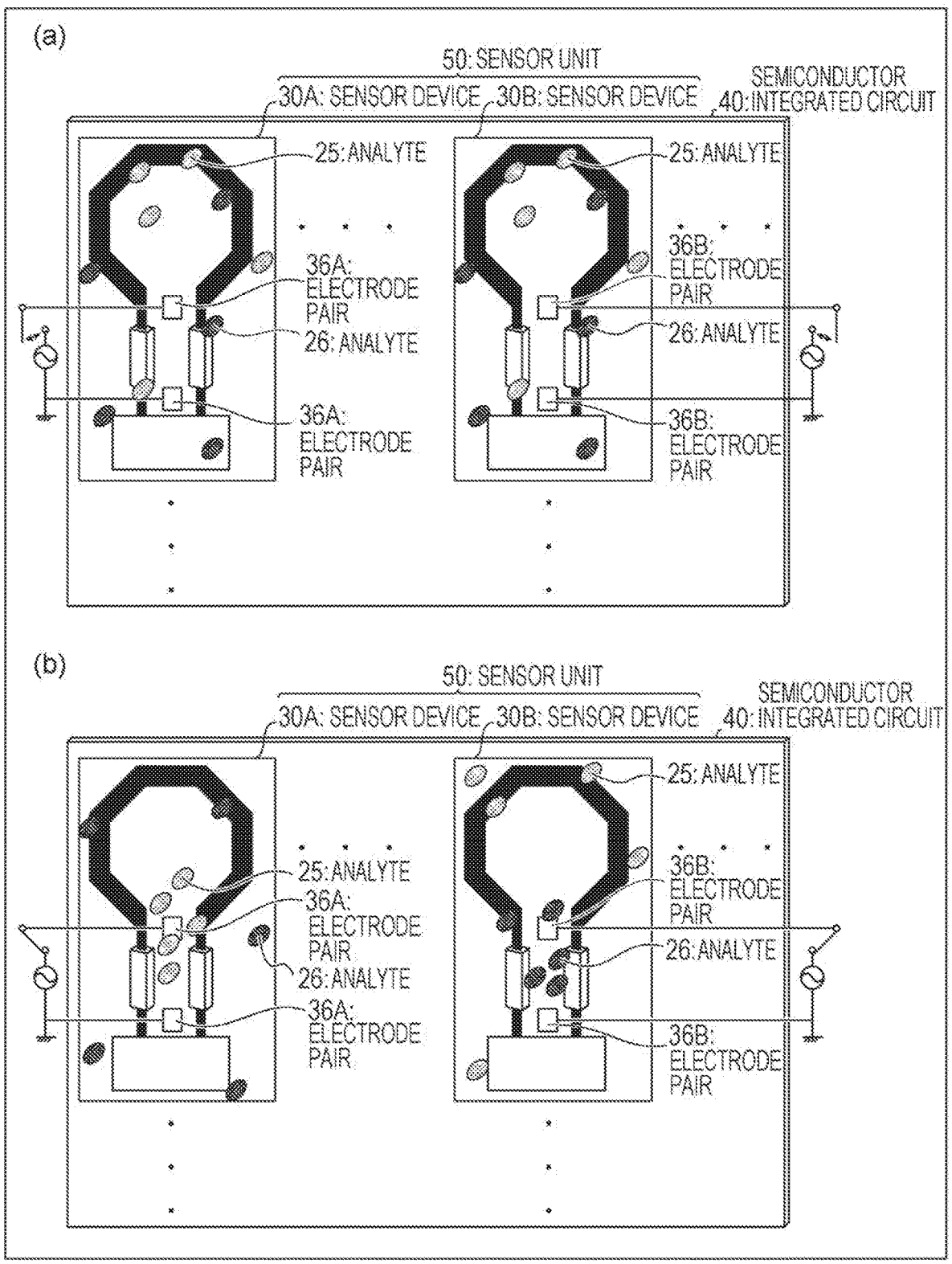
FIG. 8(a) is a view illustrating a state before an alternating-current voltage signal is applied to an electrode pair.
FIG. 8(b) is a view illustrating a state after the alternating-current voltage signal is applied to the electrode pair.

An example in which a sensor unit 50 according to the present embodiment is used in liquid containing two or more kinds of analytes dispersed therein will be described with reference to FIG. 8. FIG. 8(a) is a view illustrating a state before an alternating-current voltage signal is applied to the electrode pairs 36A, 36B, . . . , and FIG. 8(b) is a view illustrating a state after the alternating-current voltage signal is applied to the electrode pairs 36A, 36B, . . . .

First, as illustrated in FIG. 8(a), liquid (not shown here) containing two or more kinds of analytes, dielectric particles such as cells, is brought into contact with a surface of each of the sensor devices 30A, 30B, . . . . In the figures, two kinds of analytes, an analyte 24 which is a target and an analyte 25 which is a target, are dispersed in the liquid. Note that three or more kinds of analytes which are targets may be provided.

Next, the alternating-current voltage signal having an angular frequency ω is applied to the electrode pairs 36A, 36B, . . . . In the present embodiment, for the electrode pair 36A, an angular frequency ω of the alternating-current voltage signal is selected so that positive dielectrophoretic force is applied to the analyte 24, which is a target, and for the electrode pair 36B, an angular frequency ω of the alternating-current voltage signal is selected so that positive dielectrophoretic force is applied to the analyte 25, which is a target.

As illustrated in FIG. 8(b), the dielectrophoretic force generated by the alternating-current voltage signal causes pieces of the analyte 24 to be collected in the vicinity of sensing electrodes 35 of the sensor device 30A, and pieces of the analyte 25 to be collected in the vicinity of sensing electrodes 35 of the sensor device 30B. The oscillation frequency detection unit 12 of each of the sensor devices 30A, 30B, . . . in this state detects the oscillation frequency of the oscillation unit 31, and thereby, the oscillation frequency as the complex permittivity of the analyte 24 and the analyte 25, which are targets, and a change of the oscillation frequency along with a change of the complex permittivity of the analyte 21 can be selectively detected at the same time even in liquid containing a plurality of kinds of analytes which are targets.

For example, blood is liquid as blood plasma in which a plurality of types of blood cells such as erythrocytes are dispersed. The angular frequency ω of the alternating-current voltage signal is appropriately configured in accordance with the dielectric property of a plurality of types of blood cells which are targets in the blood, and then, the blood is tested by using the sensor unit 50 according to the present embodiment. In this way, the dielectric property with respect to each type of the blood cells which are the targets can simultaneously be measured simply by the sensor unit 50 according to the present embodiment without performing a component separation process such as centrifugal separation of the blood.

Note that for the sake of simplicity of the description, the operation of the sensor device 30A and the sensor device 30B of the plurality of sensor devices 30k, 30B, . . . has been described above, but other sensor devices may perform operations similar to that of the sensor devices 30A and 30B.

Fifth Embodiment (Configuration of Sensor Device)

The configuration of a sensor device according to the present embodiment is similar to that of the sensor device 30 shown in FIG. 3. Note that in the present embodiment, a direct-current voltage signal is applied to an electrode pair 36 to guide an analyte having charge deviation. Thus, unlike the first to fourth embodiments in which the dielectrophoretic force moves the analyte, in the present embodiment, the analyte does not move to the intermediate region between the electrode pair 36 but moves in a direction toward an electrode of the electrode pair to which the direct-current voltage signal is applied or in a repelling direction. Note that the direct-current voltage signal may be applied to one electrode of the electrode pair 36 or both electrodes of the electrode pair 36.

Thus, in a sensor device 30 according to the present embodiment, the electrode pair 36 may be disposed in a location similar to that of the first to fourth embodiments, but the electrode of the electrode pair 36 to which the direct-current voltage signal is applied is preferably located in an intermediate location between two plate-shaped electrodes constituting sensing electrodes 35. Moreover, in order to move more pieces of the analyte, an electrode area is preferably large so that the electrode of the electrode pair 36 to which the direct-current voltage signal is applied receives a large number of charges.

Note that similarly to the third and fourth embodiments, a sensor unit including a plurality of the sensor devices 30 according to the present embodiment may be configured.

(Operation and Effect)

Figure 9:
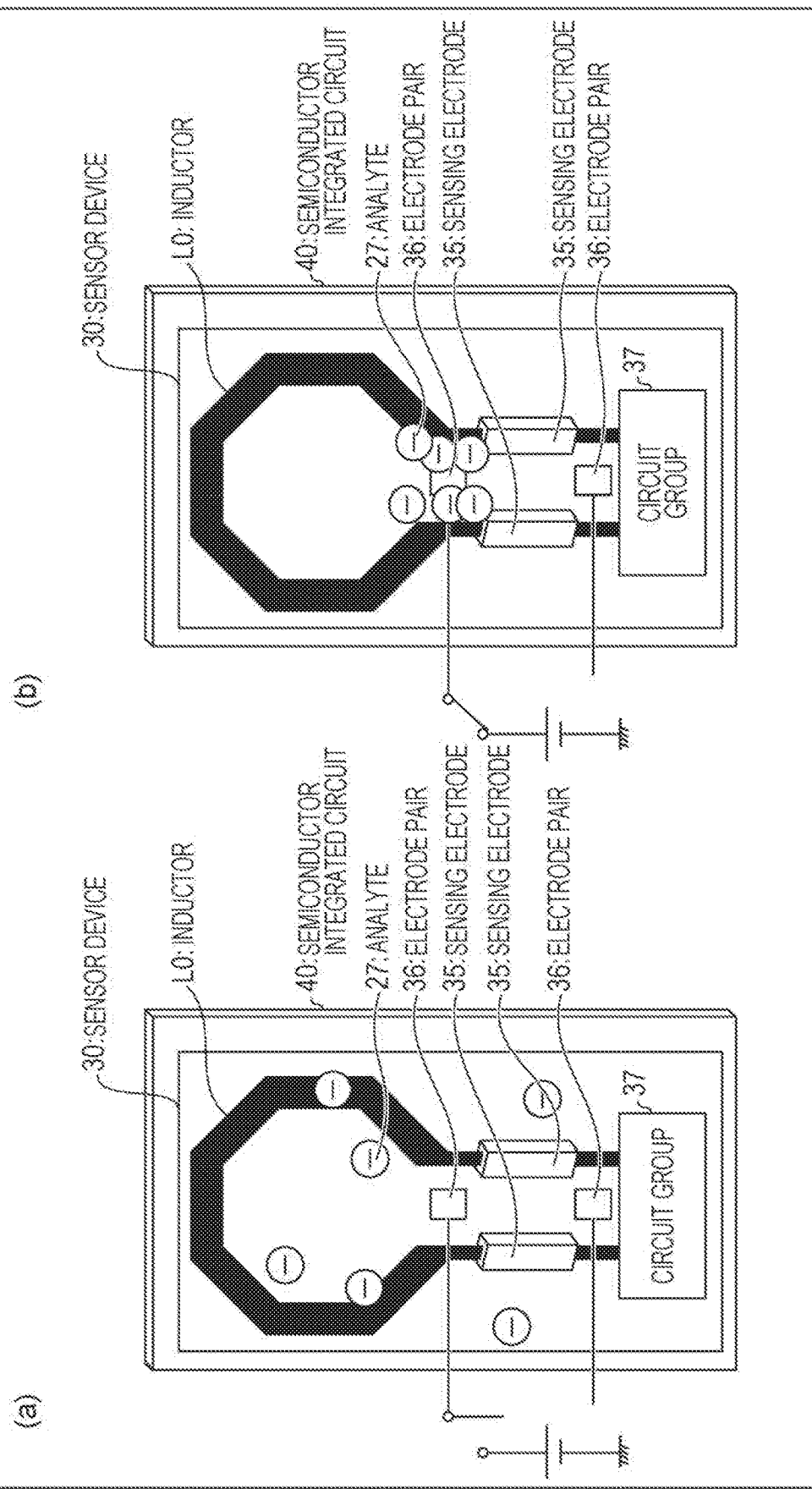
FIG. 9(a) is a view illustrating a state before a direct-current voltage signal is applied to an electrode pair.
FIG. 9(b) is a view illustrating a state after the direct-current voltage signal is applied to the electrode pair.

An example in which the sensor device 30 according to the present embodiment is used in liquid containing one kind of analyte dispersed therein will be described with reference to FIG. 9. FIG. 9(a) is a view illustrating a state before a direct-current voltage signal is applied to an electrode pair 36, and FIG. 9(b) is a view illustrating a state after the direct-current voltage signal is applied to the electrode pair 36.

First, as illustrated in FIG. 9(a), liquid (not shown here) containing one kind of analyte 27, charged particles such as ions, molecules, or DNAs, is brought into contact with a surface of the sensor device. Note that the liquid may contain an analyte which is not a target as described in the second embodiment.

Next, a direct-current voltage signal is applied to the electrode pair 36. As illustrated in FIG. 9(b), applying the direct-current voltage signal to one electrode or both electrodes of the electrode pair 36 causes the analyte 27 to be attracted to the one electrode or the both electrodes to which the direct-current voltage signal is applied. In the present drawing, negatively charged pieces of the analyte are attracted to the electrodes to which a positive direct-current voltage signal is applied, but on the contrary, positively charged pieces of the analyte may be attracted to the electrode to which a negative direct-current voltage signal is applied.

Thus, pieces of the analyte 27 are collected in the vicinity of the sensing electrodes 35. An oscillation frequency detection unit 12 in this state detects the oscillation frequency of an oscillation unit 31, and thereby, the oscillation frequency depending on the analyte 27 can selectively be measured.

Sixth Embodiment (Configuration of Sensor Device)

Figure 10:
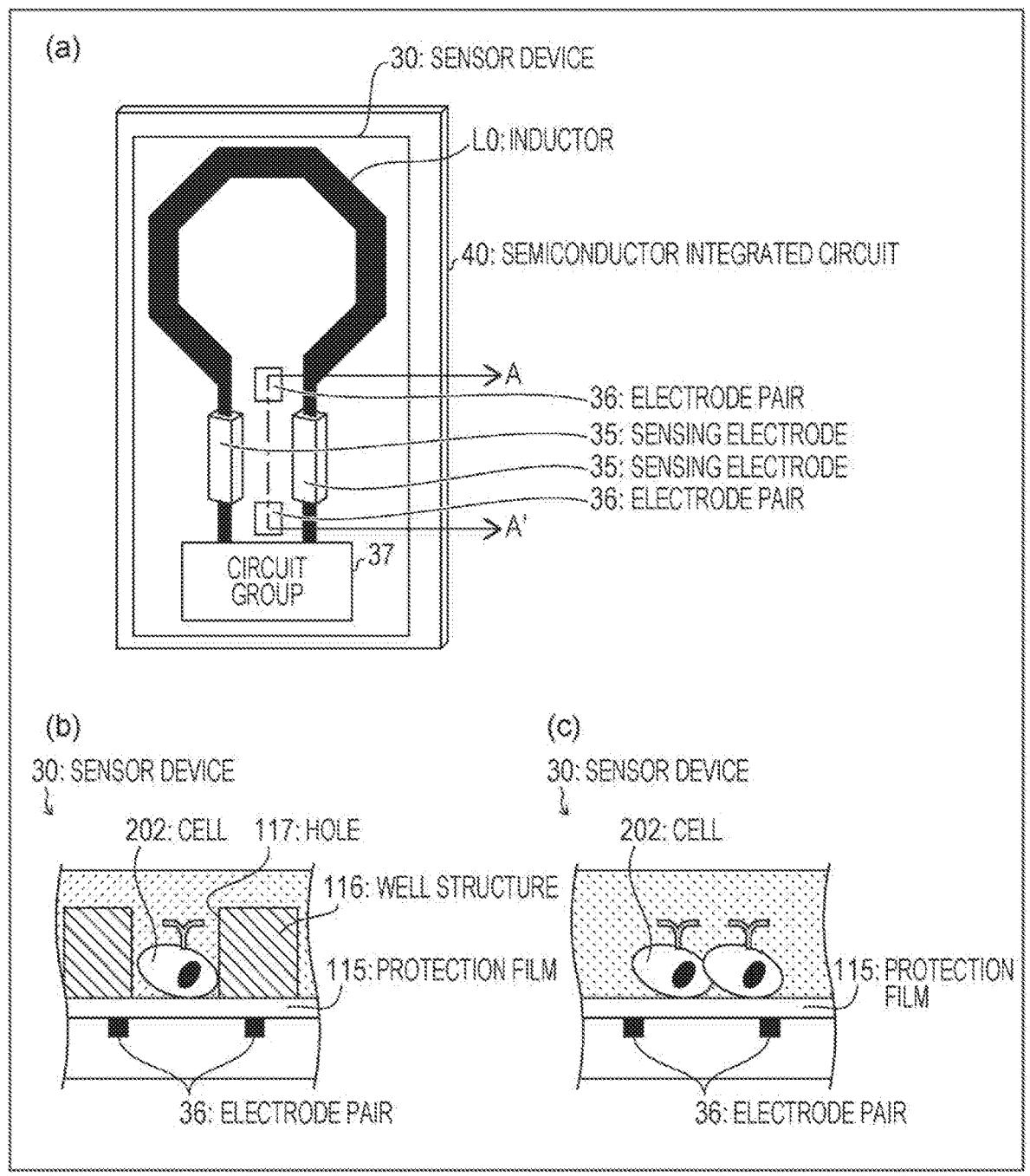
FIG. 10(a) is a view schematically illustrating a semiconductor integrated circuit in which a sensor device including an electrode pair as an analyte moving means is formed.
FIG. 10(b) is a sectional view taken along line A-A' in the arrow direction of FIG. 10(a)
FIG. 10(c) is a sectional view taken along line A-A' in the arrow direction of FIG. 10(a), wherein a well structure is not provided.

The configuration of a sensor device according to the present embodiment will be described with reference to FIG. 10. FIG. 10(a) is a view schematically illustrating a semiconductor integrated circuit 40 in which a sensor device 30 is formed, the sensor device 30 including an electrode pair 36 as an analyte moving means, FIG. 10(b) is a sectional view taken along line A-A' in the arrow direction of FIG. 10(a), and FIG. 10(c) is a sectional view taken along line A-A' in the arrow direction of FIG. 10(a), wherein a well structure is not provided.

First, as illustrated in FIG. 10(a), the configuration of a sensor device according to the present embodiment is similar to that of the sensor device 30 shown in FIG. 3. Note that in the present embodiment, the sensor device 30 has a well structure 116 made of dimethylpolysiloxane (PDMS) on a protection film 115 on the one electrode pair 36 as shown in FIG. 10(b). The well structure 116 has a hole 117 which one cell 202 enters.

The sensor device 30 can detect the presence or absence of protein in an analyte by performing processes similar to those described in the first to third embodiments.

(Effects)

In order to maintain a state where the cell 202 is captured as shown in FIG. 10(c), an alternating-current electric field has to be continuously applied to the electrode pair 36. However, when the state shown in FIG. 10(b) is achieved, the cell 202 is physically adsorbed an the well structure 116 and a captured state is maintained due to interaction between the well structure 116 and the cell 202 even when application of the alternating-current electric field to the electrode pair 36 is stopped after the cell 202 is captured.

When dielectrophoresis is performed in a sensor device which does not have the well structure 116, a plurality of cells 202 may be captured between the electrode pair 36 as shown in FIG. 10(c). However, when the well structure 116 is introduced as in the sensor device 30 according to the present embodiment, only one cell 202 is captured, and thus, it becomes possible to provide a quantitative property to the test.

Seventh Embodiment (Configuration of Sensor Device)

Figure 11:
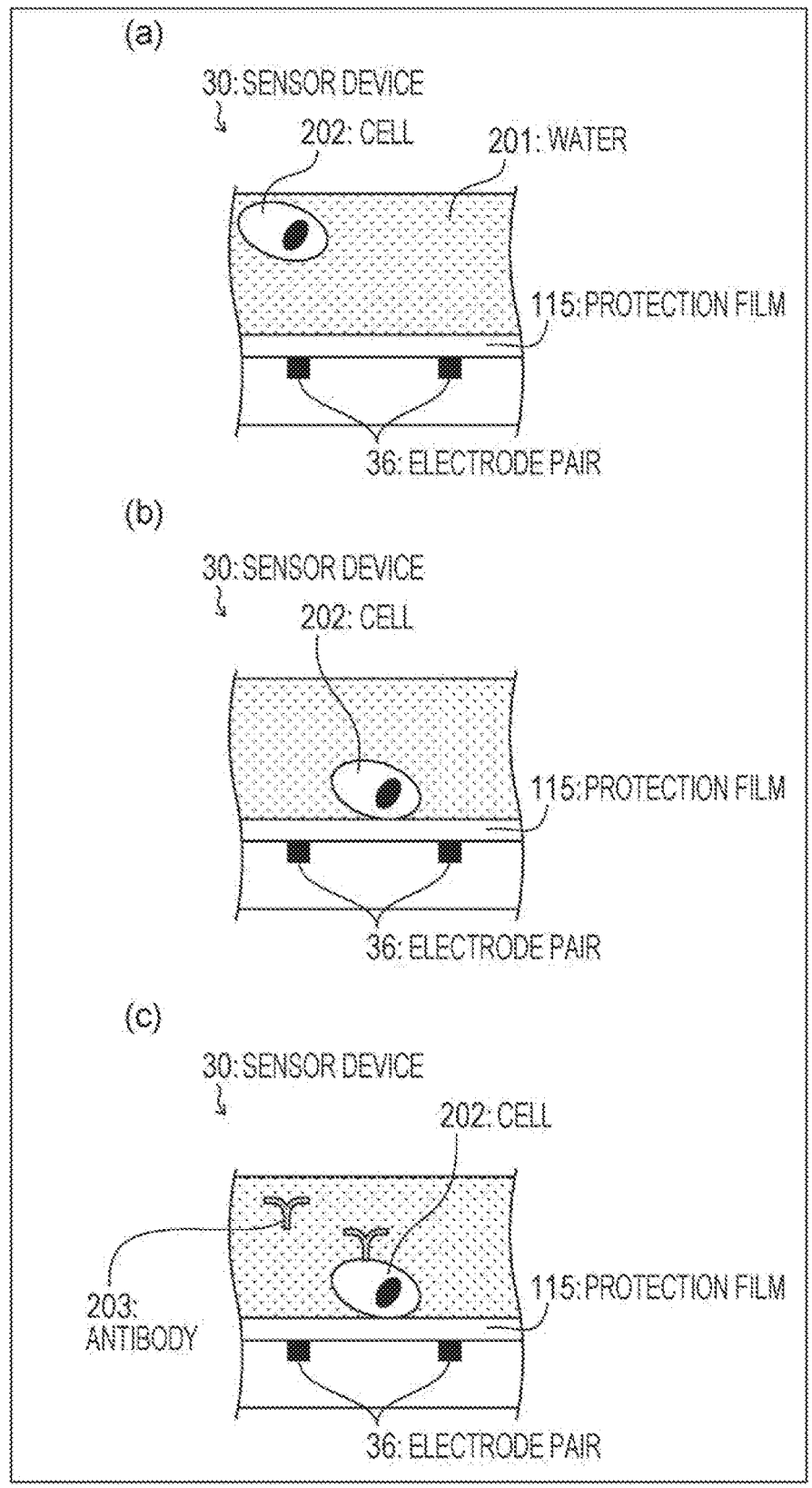
FIG. 11 is a sectional view taken along line A-A' in the arrow direction of FIG. 10(a).

The configuration of a sensor device according to the present embodiment is similar to that of the sensor device 30 shown in FIG. 3. FIG. 11 is a sectional view taken along line A-A' in the arrow direction of FIG. 10(a).

As illustrated in FIG. 11(a), in a sensor device 30, water 201 is brought into contact with a protection film 115. In the water 201, ions or the like are injected as necessary to adjust electrophoresis. Moreover, in order to prevent spilling or drying of water, a container and a flow path are made of, for example, dimethylpolysiloxane (PDMS), a resin, and silicon dioxide ($SiO_2$) as necessary.

(Operation)

As illustrated in FIG. 11(a), a cell 202 which is a second biological substance is injected into the water 201. Next, an alternating-current voltage having a voltage and a frequency at which the cell 202 is captured between an electrode pair 36 is applied to the electrode pair 36 for dielectrophoresis. Moreover, the conductivity n of the water 201 is adjusted by, for example, ion injection as necessary. Specifically, from the above-described formula (3), the voltage, the frequency, and the conductivity σ are configured so that dielectrophoretic force FDEP is in the capture direction. Thus, the cell 202 is captured between the electrode pair 36 as illustrated in FIG. 11(b).

Next, an antibody 203 which is a first biological substance is injected into the water 201. Thus, the antibody 203 is adsorbed on the cell 202 and fixed to a sensor surface between the electrode pair 36. This is the same as that the antibody 203 is fixed to the sensor surface between sensing electrodes 35.

(Protein Test)

Figure 12:
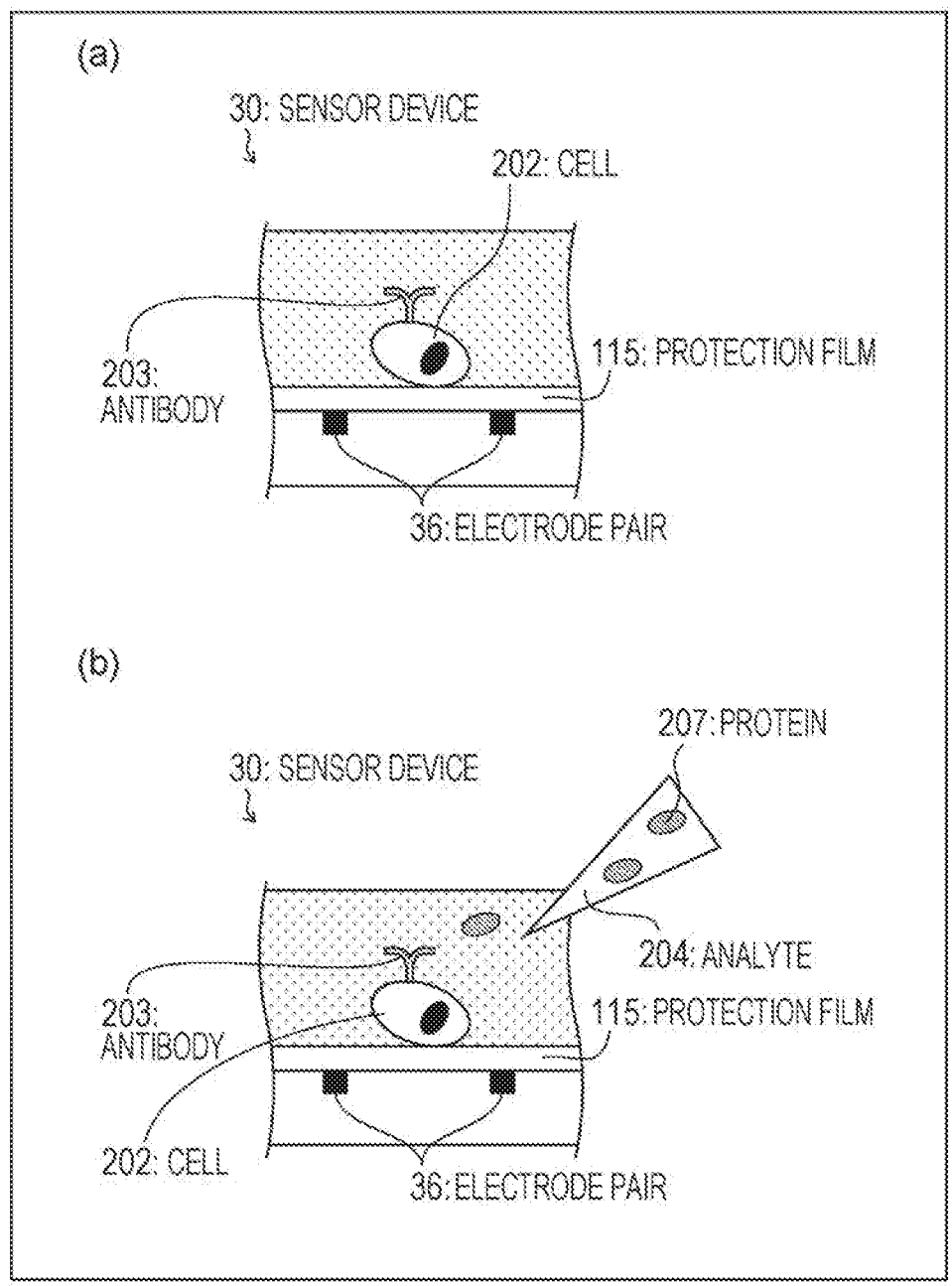
FIG. 12 is a sectional view taken along line A-A' in the arrow direction of FIG. 10(a).
Figure 13:
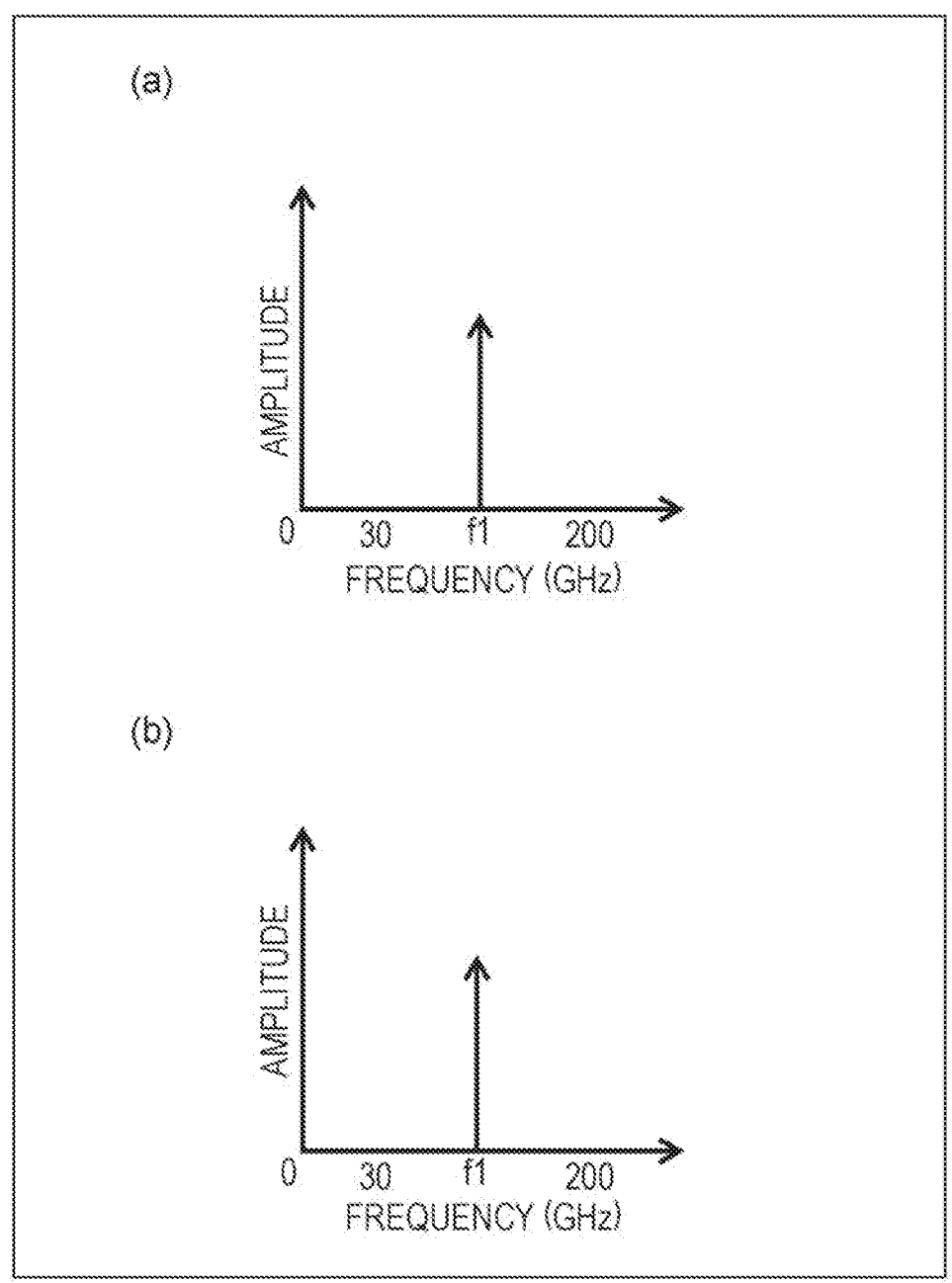
FIG. 13 is a view illustrating an oscillation frequency of an oscillation unit, the oscillation frequency being detected by an oscillation frequency detection unit.
Figure 14:
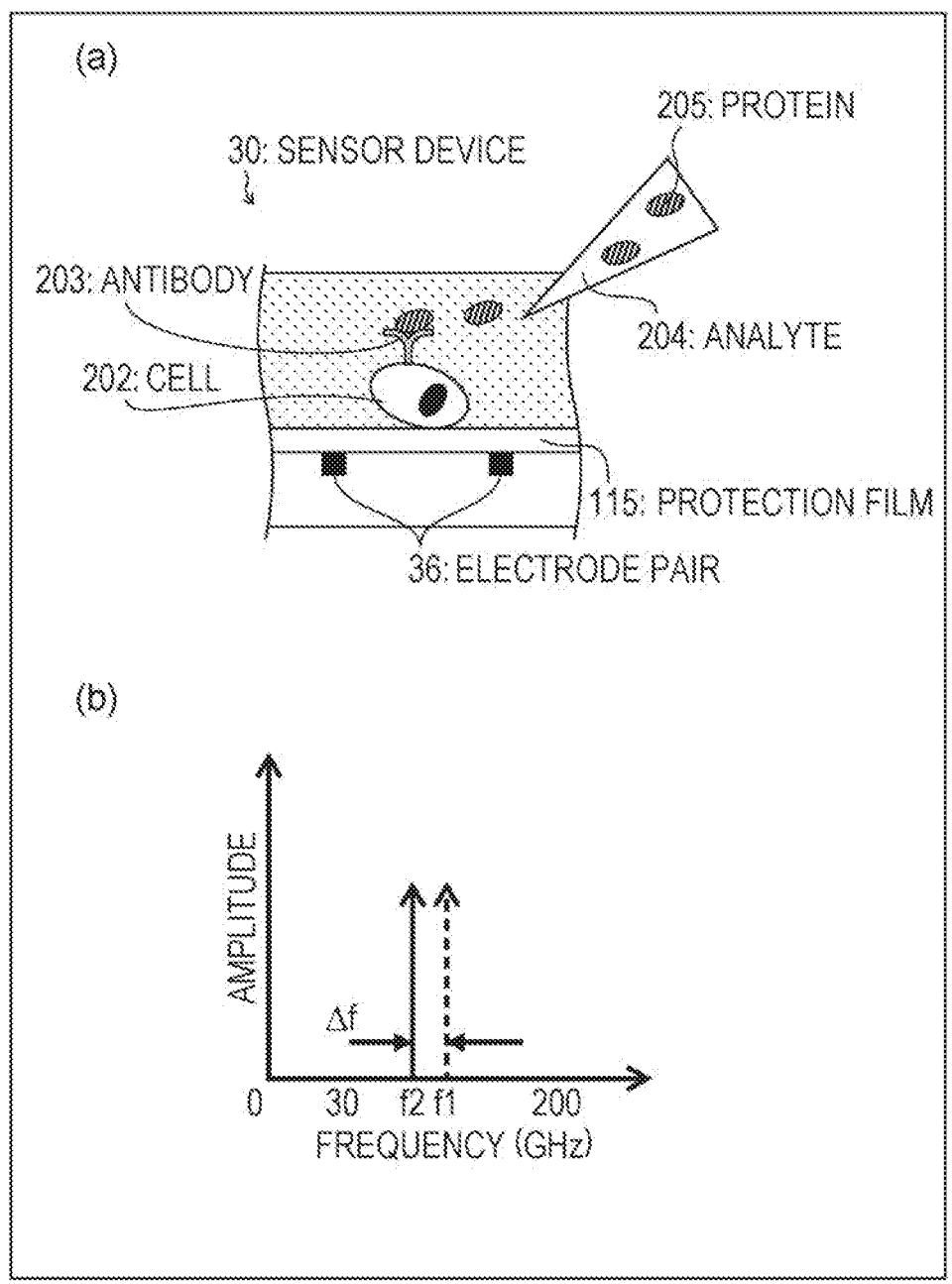
FIG. 14(a) is a sectional view taken along line A-A' in the arrow direction of FIG. 10(a)
FIG. 14(b) is a view illustrating as oscillation frequency of as oscillation unit, the oscillation frequency being detected by an oscillation frequency detection unit.

A protein test by using the sensor device 30 according to the present embodiment will be described with reference to FIGS. 12 to 14. FIG. 12 is a sectional view taken along line A-A' in the arrow direction of FIG. 10(a). FIG. 13 is a view illustrating the oscillation frequency of an oscillation unit 31, the oscillation frequency being detected by an oscillation frequency detection unit 32. Moreover, FIG. 14(a) is a sectional view taken along line A-A' in the arrow direction of FIG. 10(a), and FIG. 14(b) is a view illustrating the oscillation frequency of an oscillation unit 31, the oscillation frequency being detected by an oscillation frequency detection unit 32.

As shown in FIG. 12(a), a dielectric property is measured in a state where the antibody 203 is fixed to the sensor surface by the above-described method. The oscillation frequency detection unit 32 detects an oscillation frequency f1 of the oscillation unit 31 in a state shown in FIG. 12(a) (FIG. 13(a)).

Next, as shown in FIG. 12(b), an analyte 204 containing protein 207 is injected into the water 201 in contact with the sensor device 30, and the dielectric property is measured. The oscillation frequency detection unit 32 then detects an oscillation frequency f2 of the oscillation unit 31 in a state shown in FIG. 12(b).

Here, as illustrated in FIG. 12(b), when protein which is a target of antigen-antibody reaction with the antibody 203 is not present in the analyte 204 (that is, when the protein 207 is not the protein which is a target of antigen-antibody reaction with the antibody 203), the sensor device 30 remains in the state shown in FIG. 12(a), and the oscillation frequency f2 of the oscillation unit 31 remains f1 (FIG. 13(b)).

On the other hand, when protein 205 which is a third biological substance serving as a target of the antibody 203 is present in the analyte 204, the sensor device 30 is in the state as shown in FIGS. 12(a) to 14(a). Thus, the permittivity of the water 201 changes.

When the relative complex permittivity $\varepsilon = \varepsilon r - j\varepsilon i$ changes as described above, the oscillation frequency fres changes based on the above-described formula (2). That is, when the protein 205 which is the third biological substance serving as a target of the antigen-antibody reaction with the antibody 203 is present in the analyte 204, $f2 \neq f1$ (FIG. 14(b)).

The oscillation frequency f1 of the oscillation unit 31 before injection of the analyte 204 into the water 201 in contact with the protection film 115 and the oscillation frequency f2 of the oscillation unit 31 after the injection are detected by the oscillation frequency detection unit 32, and if $f2 \neq f1$, it is possible to determine that the protein 205 as the third biological substance is present in the analyte 204, and if $f2 = f1$, it is possible to determine that the protein 205 as the third biological substance is not present in the analyte 204.

(Effects)

A user compares the oscillation frequency f1 of an oscillator before the injection of the analyte 204 with the oscillation frequency 2 after the injection, which enables the user to determine whether or not the protein 205 is present in the analyte 204.

The cells 202 are captured at a desired location through dielectrophoresis, and the antibody 203 is adsorbed on the cell 202, which enables the antibody 203 to selectively be fixed to a desired location on the sensor surface. Thus, the antibody 203 is selectively fixed to only a location with high sensing sensitivity of the sensor device 30, and thereby, it becomes possible to effectively increase the sensing sensitivity of the protein 205.

(Limitation Release)

For example, when the antibody 203 is an anti-ovalbumin antibody, use of the sensor device 30 circuit according to the present embodiment enables a food allergen test for determining whether or not ovalbumin serving as main protein constituting egg white is present in the analyte 204. Note that the antibody 203 is not limited to the anti-ovalbumin antibody but may be an antibody for capturing other proteins such as whey or casein.

Moreover, when the antibody 203 is an anti-A antibody, it is possible to detect whether or not an A antigen present in an erythrocyte surface in each of type A blood and type AB blood is present in the analyte 204. Note that the antibody 203 is not limited to the anti-A antibody but may be an anti-B antibody.

Moreover, the water 201 is not limited to water but may be other liquid such as phosphate-buffered saline (PBS) as long as it does not inhibit antibody-antigen reaction between the antibody 203 and the protein 205.

Eighth Embodiment (Configuration of Sensor Device)

The configuration of a sensor device according to the present embodiment is similar to that of the sensor device 30 shown in FIG. 3.

(Operation)

In the present embodiment, a cell 202 which serves as a second biological substance and on which an antibody 203 serving as a first biological substance is adsorbed is prepared is advance, and the cell 202 is injected in water 201. In this way, as illustrated in FIG. 12(a), selective fixation of the cell 202, on which the antibody 203 is adsorbed, to a sensor surface is possible simply by a dielectrophoresis process.

Next, similarly to the first embodiment, the oscillation frequency f1 of an oscillation unit 31 before injection of an analyte 204 into water 201 in contact with a protection film 115 and the oscillation frequency f2 after the injection are detected by an oscillation frequency detection unit 32. In f2≠f1, it is possible to determine that the protein 205 as the third biological substance is present in the analyte 204, and if f2=f1, it is possible to determine that the protein 205 as the third biological substance is not present in the analyte 204.

(Effects)

Preparing the cell 202, on which the antibody 203 is adsorbed, in advance enables a configuration similar to that of the first embodiment to be realized simply by the dielectrophoresis process. That is, an effect similar to that of the first embodiment is obtained simply by the dielectrophoresis process.

Ninth Embodiment (Configuration of Sensor Device)

The configuration of a sensor device according to the present embodiment is similar to that of the sensor device 30 shown in FIG. 3.

(Operation)

A protein test by using a sensor device 30 according to the present embodiment will be described with reference to FIGS. 15 and 16. FIG. 15 is a sectional view taken along line A-A' in the arrow direction of FIG. 10(a). FIG. 16 is a view illustrating the oscillation frequency of an oscillation unit 31, the oscillation frequency being detected by an oscillation frequency detection unit 32.

In the present embodiment, as a cell 202 serving as a second biological substance, a mast cell is used, and a process similar to that of the first or second embodiment is performed, thereby achieving a state where the cell 202, on which an antibody 203 is adsorbed, is selectively fixed to a sensor surface as illustrated in FIG. 15(a).

Next, similarly to the first embodiment, the oscillation frequency f1 of the oscillation unit 31 before injection of an analyte 204 into water 201 in contact with a protection film 115 and the oscillation frequency f2 after the injection are detected by the oscillation frequency detection unit 32 (FIG. 16). If f2≠f1, it is possible to determine that the protein 205 as the third biological substance is present in the analyte 204, and if f2=f1, it is possible to determine that the protein 205 as the third biological substance is not present in the analyte 204.

(Effects)

According to NPL 3 mentioned above, when the antibody 203 adsorbed on the mast cell causes antibody-antigen reaction with the protein 205, the mast cell is activated, and the refractive index distribution and permittivity distribution of the entire cell changes. Moreover, when the mast cell is activated, histamine 206 is released as illustrated in FIG. 15(b).

In the case of the first or second embodiment, a range within which the permittivity changes due to the antibody-antigen reaction is on the order of several tens of nanometers which is the same as the size of the antibody 203 or the protein 205. In contrast, in the present embodiment, the range within which the permittivity changes due to the antibody-antigen reaction is drastically increased, that is, on the order of several micrometers which is the same as the size of the cell 202, and thus, detection by the sensor device 30 becomes easy. That is, the sensing sensitivity of the sensor device 30 to the protein 205 is significantly increased.

(Limitation Release)

The cell 202 is not limited to the mast cell. The cell 202 may be other cells, for example, a basophil as long as antibody-antigen reaction of the antibody 203 adsorbed on the cell 202 activates the entire cell 202 and changes the refractive index and the permittivity or releases histamine.

Tenth Embodiment (Configuration of Sensor Device)

Figure 17:
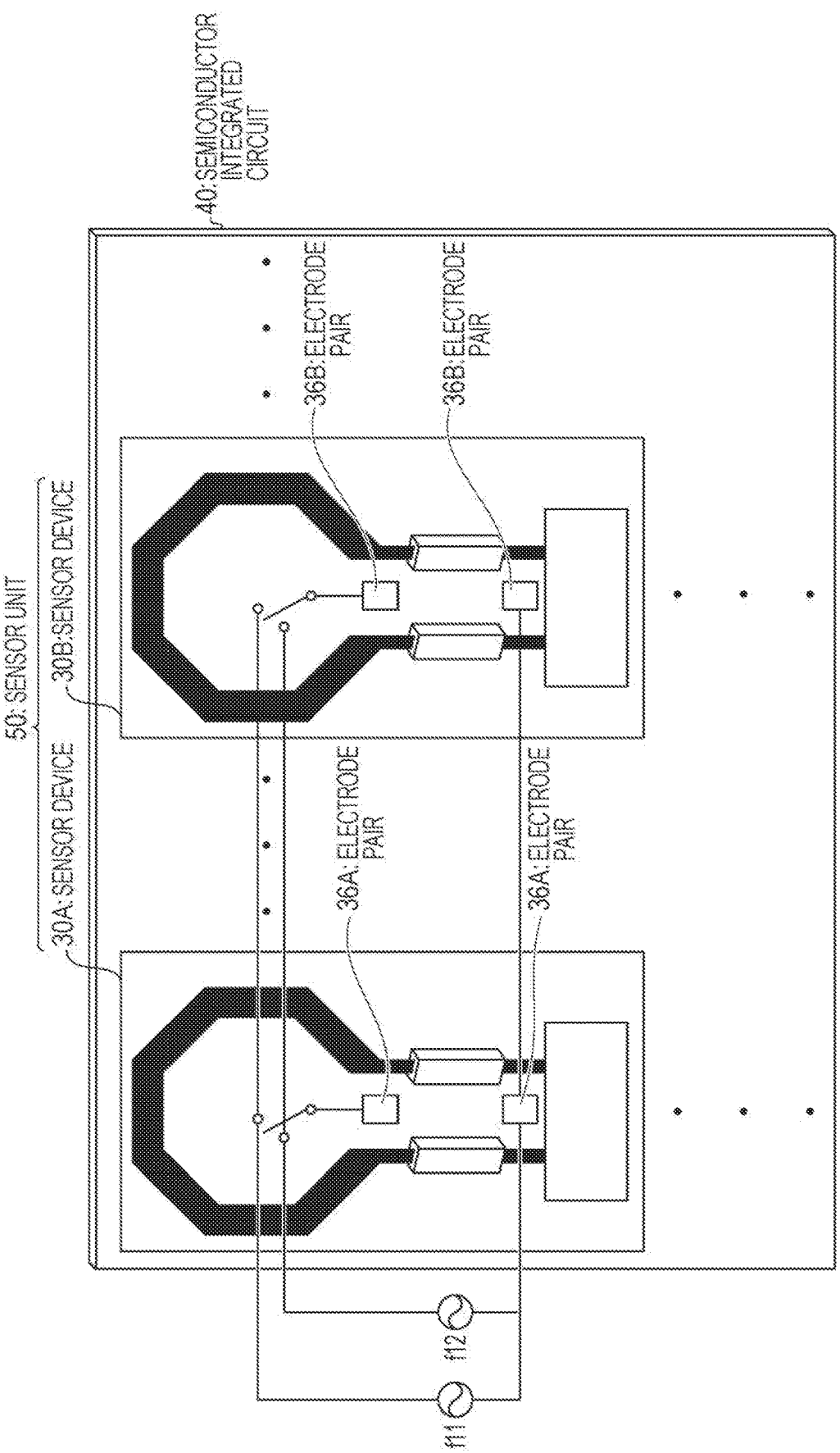
FIG. 17 is a view schematically illustrating a semiconductor integrated circuit in which a sensor unit is formed.

With reference to FIG. 17, the configuration of the sensor unit according to the present embodiment will be described. FIG. 17 is a view schematically illustrating a semiconductor integrated circuit 40 in which a sensor unit 50 is formed.

As illustrated in FIG. 17, a sensor unit according to the present embodiment has a configuration similar to that of the sensor snit 50 shown in FIG. 6. Note that electrode pairs 36A, 36B, . . . are independently connectable to alternating-current power supplies of frequencies f11 and f12.

Note that a sensor unit may have a configuration including a well structure which is similar to that of the sixth embodiment and which is provided on each oscillation unit. In particular, in a structure in which each oscillation unit captures only one cell, the well structure is preferably provided. Note that the well structure is not shown in FIG. 17 in order to avoid complication of the drawing.

(Operation)

The alternating-current power supply is configured such that the frequency f11 is a frequency at which dielectrophoretic force is exerted in a direction in which the cell is captured. The alternating-current power supply is configured such that the frequency f12 is a frequency at which the dielectrophoretic force is exerted in a direction in which the cell is released.

First, none of the electrode pairs 36A, 36B, . . . is connected to the alternating-current power supply, or all the electrode pairs 36A, 36B, . . . are connected to the alternating-current power supply of the frequency f12. Thus, the dielectrophoretic force is not exerted, or the dielectric force is exerted in a direction in which the cell is released. In this state, a cell is captured by none of the oscillation units. In this state, the oscillation frequencies f0A, f0B, . . . of all the oscillation units are measured.

Next, all the electrode pairs 36A, 36B, . . . are connected to the alternating-current power supply of the frequency f11. Thus, the dielectrophoretic force is exerted in a direction in which the cell is captured. In this state, a cell 202 to which an antibody 203 is added is introduced into water 201 in contact with a protection film 115, and dielectrophoresis process similar to that of the first or second embodiment is performed.

Subsequently, the oscillation frequencies f1A, f1B, . . . of all the oscillation units are measured. As a result, for the oscillation unit of the sensor device 30A, if f0A=f1A, it is determined that the cell 202 is not captured by the oscillation unit, and if f0A≠f1A, it is determined that the cell 202 is captured by the oscillation unit. Until it is determined that the cell is captured, the electrode pair 36A is connected to the alternating-current power supply of the frequency f11. The same is performed on the other oscillation units to confirm that all the oscillation units capture cells 202 and the antibodies 203 are fixed.

After it is confirmed for all the oscillation units that the antibodies 203 are fixed, each oscillation unit is subjected to a process of maintaining connection of the alternating-current power supply of the frequency f11 to the electrode pair 36A or a process of disconnecting the electrode pair 36A from the alternating-current power supply.

After fixation of the antibody 203, in a similar manner to the fifth embodiment, the oscillation frequency f1A of the oscillation unit of the sensor device 30A before injection of an analyte 204 into the water 201 in contact with the protection film 115 and the oscillation frequency f2A after the injection are detected by the oscillation frequency detection unit 32. If f2A≠f1A, it is determined that the protein 205 is present in the analyte 204, and if f2A=f1A, it is determined that the protein 205 is not present in the analyte 204. The same process is performed on the other oscillation units.

(Effects)

Similarly to the sixth embodiment, discrete quantification of the concentration of the protein 205 in units of the number of the antibodies 203 added to the cell 202 becomes possible. This process is performed after the fixation of the antibody 203 is confirmed, thereby improving reliability of the quantification of the test.

(Limitation Release)

In the above description, it is confirmed that the antibodies 203 are fixed to all the oscillation units, and then, the process proceeds to the protein test. However, the antibodies 203 are not necessarily fixed to all the oscillation units. After confirming that the antibodies 203 are fixed to at least a predetermined number of oscillation units, the process may proceed to the protein test. In this case, the protein test is conducted only in the oscillation units to which fixation of the antibodies 203 is confirmed.

Moreover, in the above description, oscillation frequencies of the oscillation unit before and after the electrophoresis are compared with each other, but one oscillation unit may be regarded as a reference. For example, only the electrode pair 36B is not connected to the alternating-current power supply or is connected to an alternating-current power supply of the frequency f12. Thus, the cell 202 to which the antibody 203 is added is not captured by the oscillation unit of the sensor device 30B.

In this state, all the electrode pairs except for the electrode pair 36B is connected to the alternating-current power supply of the frequency f11, and the cell 202 to which the antibody 203 is added is introduced into the water 201 which is in contact with the protection film 115. The oscillation frequencies f1A and f1B of the oscillation unit 31A of the sensor device 30A and the oscillation unit 31B of the sensor device 30B are measured, and if f1A=f1B, it is determined that the cell 202 is not captured by the oscillation unit of the sensor device 30A, and if f1A≠f1B, it is determined that the cell 202 is captured by the oscillation unit of the sensor device 30A. This may be performed on all the oscillation units except for the oscillation unit of the sensor device 30B or on at least a prescribed number of oscillation units to fix the antibodies 203.

Moreover, the reference is not limited to one oscillation unit, but a plurality of oscillation units may be used as references to increase the accuracy.

Eleventh Embodiment (Configuration of Sensor Device)

Figure 18:
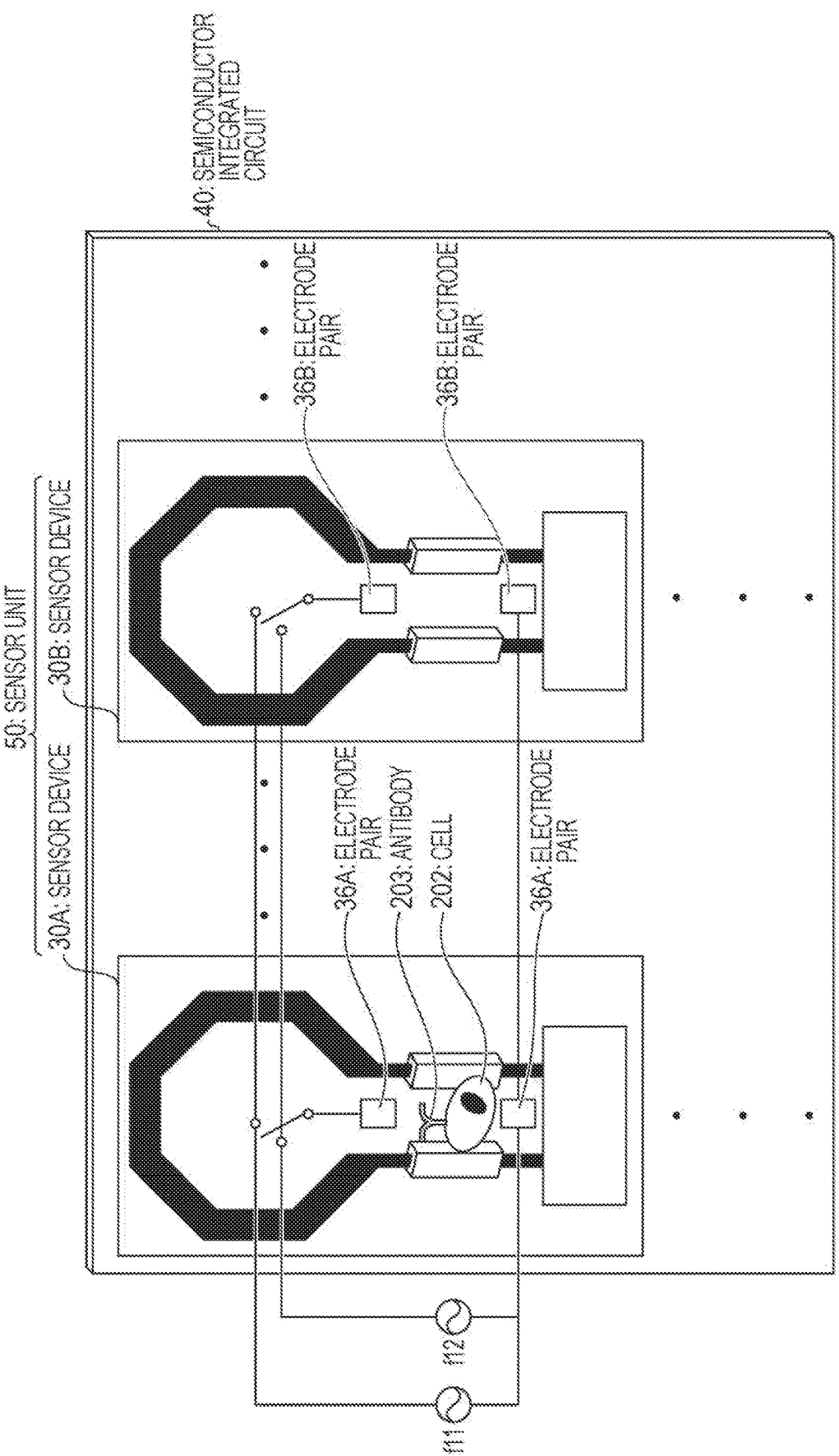
FIG. 18 is a view schematically illustrating a semiconductor integrated circuit in which a sensor unit is formed.
Figure 19:
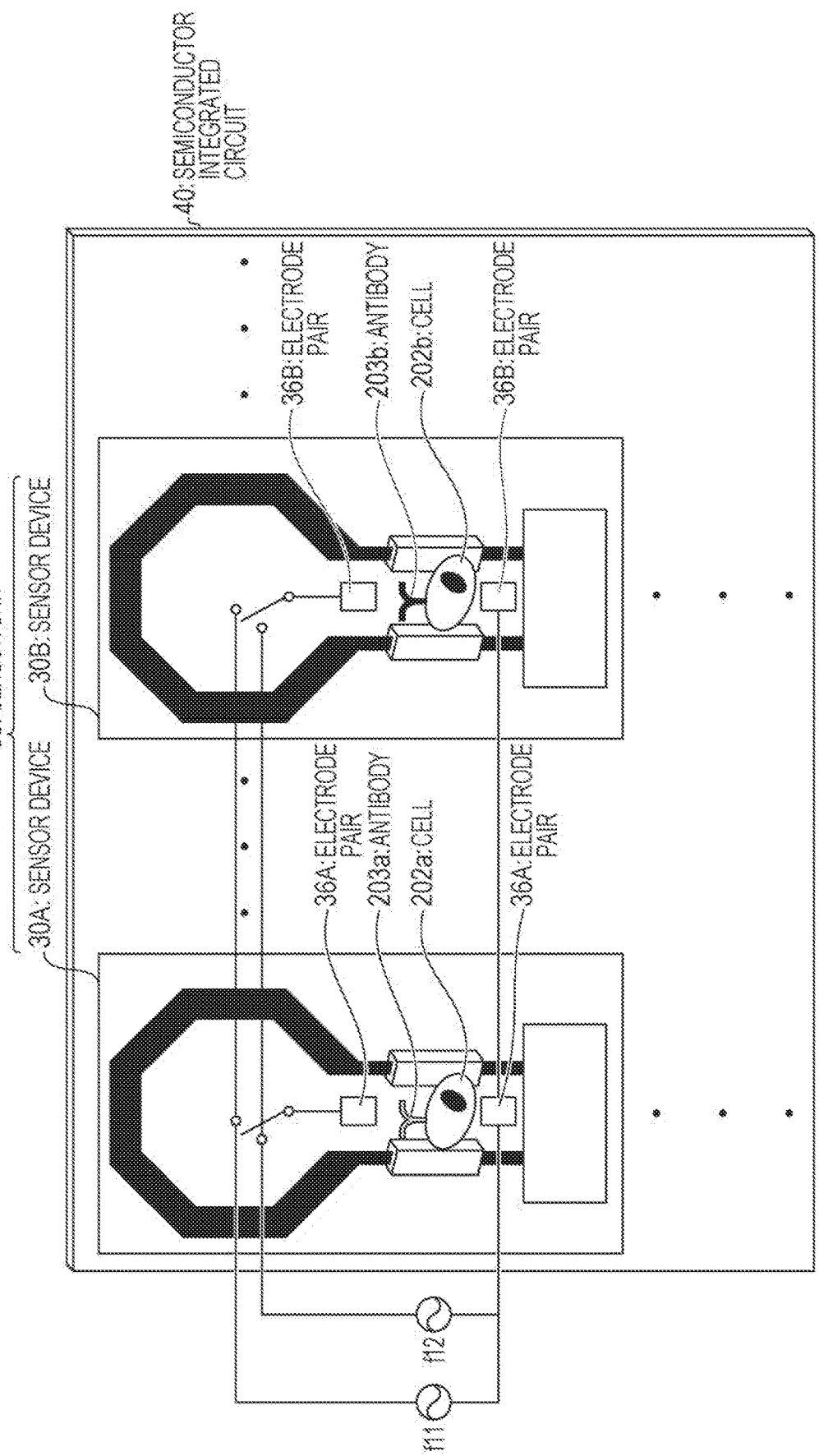
FIG. 19 is a view schematically illustrating the semiconductor integrated circuit in which the sensor unit is formed.
Figure 20:
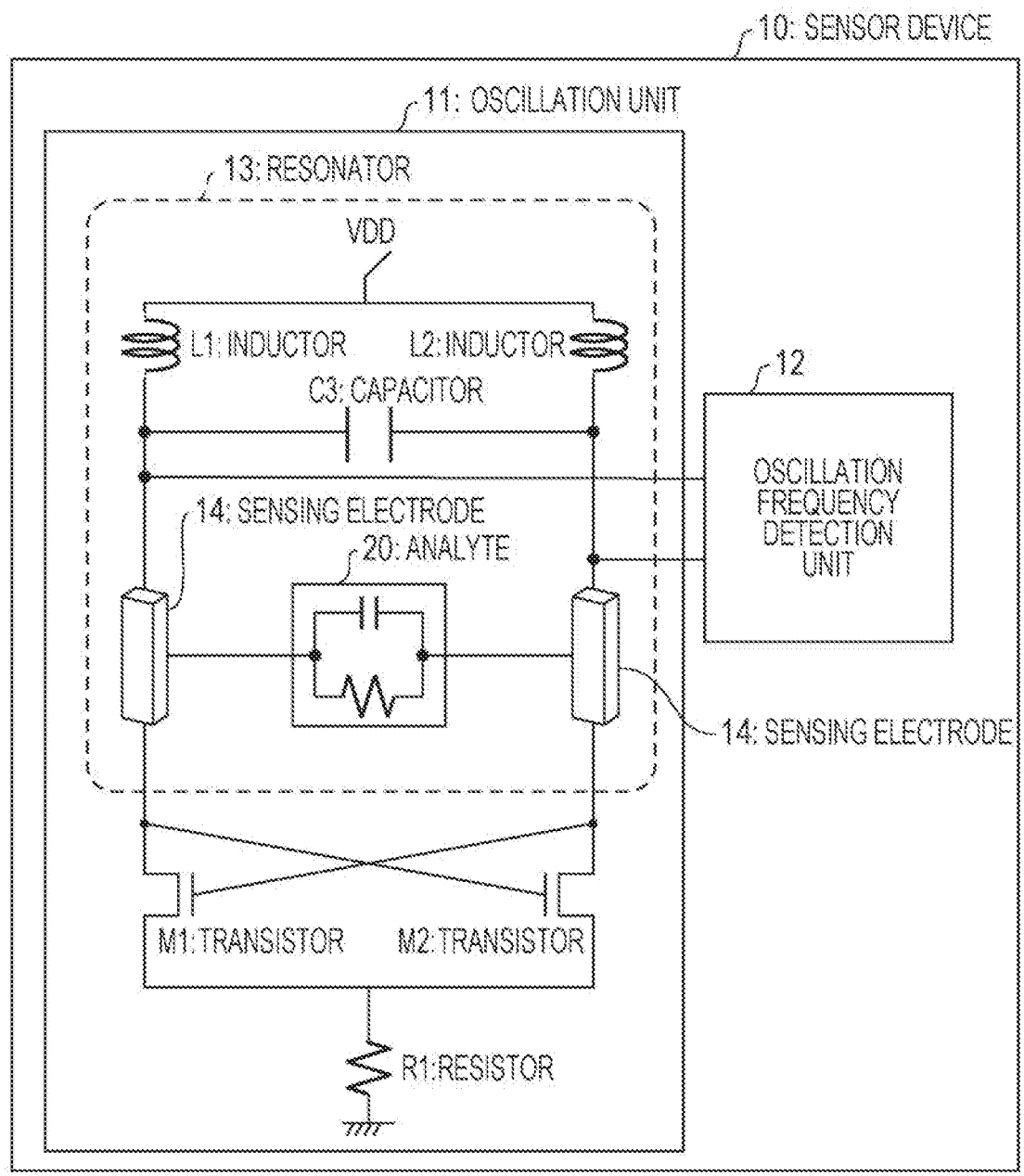
FIG. 20 is a block diagram illustrating a configuration of a conventional sensor device.
Figure 21:
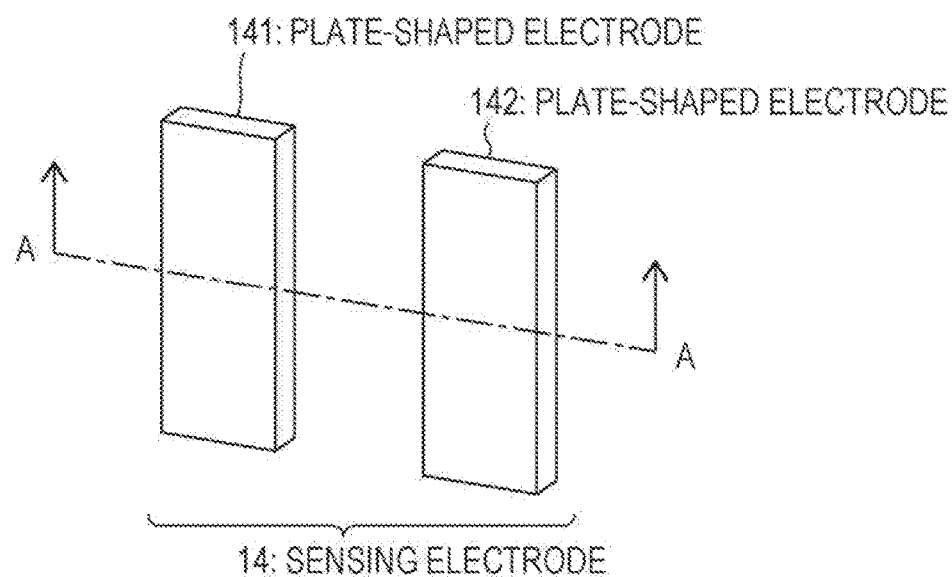
FIG. 21 is a perspective view illustrating two sensing electrodes.
Figure 22:
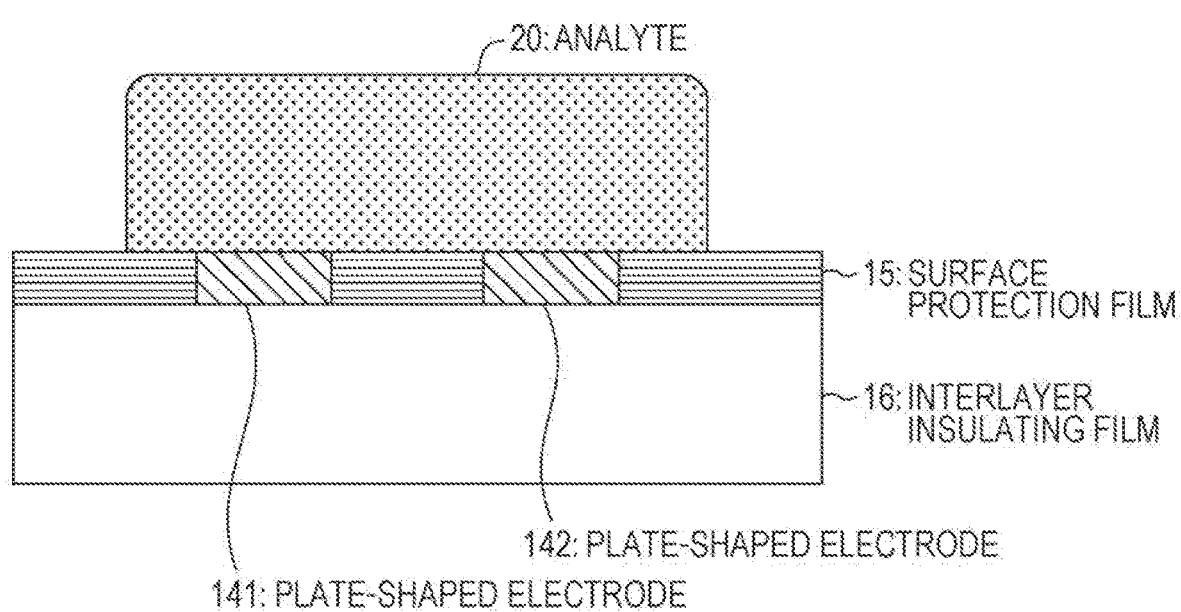
FIG. 22 is a sectional view illustrating plate-shaped electrodes and peripheral members taken along line A-A in the arrow direction of FIG. 21.

With reference to FIGS. 18 and 19, the configuration of the sensor unit according to the present embodiment will be described. FIGS. 18 and 19 are views schematically illustrating a semiconductor integrated circuit 40 in which a sensor unit 50 is formed.

As illustrated in FIGS. 18 and 19, a sensor unit according to the present embodiment has a configuration similar to that of the sensor unit 50 shown in FIG. 6. Note that electrode pairs 36A, 36B, . . . are independently connectable to alternating-current power supplies of frequencies f11 and f12.

Note that a sensor unit may have a configuration including a well structure which is similar to that of the sixth embodiment and which is provided on each oscillation unit. In particular, in a structure in which each oscillation unit captures only one cell, the well structure is preferably provided. Note that the well structure is not shown in FIGS. 18 and 19 in order to avoid complication of the drawing.

(Operation)

First, as illustrated in FIG. 18, the electrode pair 36A is connected to an alternating-current power supply of the frequency f11. Electrode pairs except for the electrode pair 36A are not connected to the alternating-current power supply or are connected to an alternating-current power supply of the frequency 112. In this state, only the electrode pair 362 captures a cell, and the other electrode pairs do not capture cells.

In this state, a cell 202A to which an antibody 203A is added is introduced into water 201 in contact with a protection film 115. Until the method described in the sixth embodiment confirms that the cell 202A is captured by the electrode pair 36A, connection of the alternating-current power supply of the frequency f11 to the electrode pair 36A is maintained.

When it is confirmed that the cell 202A is captured by the electrode pair 36A, the electrode pair 36A is detached from the alternating-current power supply, and the cell 202A, to which the antibody 203A is added, is removed from the water 201 in contact with the protection film 115.

Next, as illustrated in FIG. 19, the electrode pair 36B is connected to the alternating-current power supply of the frequency f11, and the cell 202B5 to which an antibody 203B is added is introduced into the water 201 in contact with the protection film 115. Until the method described in the sixth embodiment confirms that the cell 202B is captured by the electrode pair 36B, connection of the alternating-current power supply of the frequency f11 to the electrode pair 365 is maintained.

The above-described process is repeated, and thereby, a plurality of kinds of antibodies 203A, 203B, . . . can be fixed to respective oscillation units.

In this state, in a similar manner to the sixth embodiment, the oscillation frequency f1 of the oscillation unit 31 before injection of the analyte 204 into the water 201 in contact with the protection film 115 and the oscillation frequency f2 after the injection are detected by the oscillation frequency detection unit 32. For the oscillation unit of the sensor device 30A, if f2A≠f1A, it is possible to determine that protein 205A which is a target of the antibody 203A is present in the analyte 204, and if f2A=f1A, it is determined that the protein 205A which is the target of the antibody 203A is not present in the analyte 204.

Moreover, for the oscillation unit 31B of the sensor device 308, if f2B≠f1B, it is possible to determine that the protein 205B which is a target of the antibody 203B is present in the analyte 204, and if f2B=f1B, it is determined that the protein 205B which is the target of the antibody 203B is not present in the analyte 204.

(Effects)

Thus, a protein test by using a plurality of antibodies 203A, 203B, . . . with the same analyte 204 becomes possible. For example, it is assumed that the antibody 203A is an anti-casein antibody, and the antibody 203B is an anti-whey antibody. In this case, the presence or absence of each of casein and whey which are proteins contained in milk in the analyte 204 can be detected by a single sensor unit 50.

Moreover, for example, it is assumed that the antibody 203A is an anti-A antibody, and the antibody 203B is an anti-B antibody. In this case, the presence or absence of an A antigen and a B antigen in the analyte 204 can be detected, and thus, for example, an ABO blood test can be performed by a single sensor unit 50.

Twelfth Embodiment

In a sensor unit including a plurality of sensor devices, only an electrode pair of an oscillation unit of one sensor device is always connected to an alternating-current power supply of a frequency f12. This state is maintained and the processes of the sixth to eleventh embodiments may be performed by other oscillation units.

(Effects)

Since the electrode pair of an oscillation unit of one sensor device is always connected to the alternating-current power supply of the frequency f12, cells are not captured. Thus, a state where only water 201 is constantly measured is achieved, and thus, it becomes possible to use the oscillation unit as a reference value of a frequency measurement, and measurement accuracy can be increased.

Summary

A sensor device 30 according to a first aspect of the present invention includes: an oscillation unit 31 formed in a semiconductor integrated circuit 40 and having an oscillation frequency which changes in accordance with a physical property of an analyte which comes into contact with the oscillation unit 31; an oscillation frequency detection unit 32 configured to detect the oscillation frequency; and one or more electrode pairs 36 configured to move a specific analyte dispersed in liquid to an arbitrary location.

With this configuration, dielectrophoretic force or electrophoresis force generated by applying a voltage signal to the electrode pair 36 can be used to move the analyte to the arbitrary location. For example, the voltage signal is applied to the electrode pair 36 to move the analyte to the vicinity of sensing electrodes 35 of the oscillation unit 31, which enables the detection sensitivity of the sensor device 30 to the analyte to be improved.

As described above, when the sensor device 30 according to the one aspect of the present invention is used, the detection sensitivity to an analyte as a target dispersed in liquid can be easily improved simply by using the electrode pair 36.

In a sensor device 30 according to a second aspect of the present invention referring to the first aspect, the oscillation unit 31 includes sensing electrodes 35 which are electrodes in a pair, and the arbitrary location to which the electrode pair 36 moves the specific analyte is preferably an intermediate location between the pair of electrodes.

Influence of an oscillation frequency detection unit 12 over a detection frequency is mainly caused due to the presence of the analyte present in the intermediate location between the pair of electrodes constituting the sensing electrodes 35. Thus, according to the configuration, the analyte is moved to the intermediate location between the pair of electrodes constituting the sensing electrodes 35, which enables the oscillation frequency of the oscillation unit 31 to be detected with high sensitivity.

In a sensor device 30 according to a third aspect of the present invention referring to the second aspect, the electrode pair 36 and the sensing electrodes 35 are preferably formed in a top metal layer of the semiconductor integrated circuit 40.

With this configuration, since the electrode pair 36 and the sensing electrodes 35 are integrated into the semiconductor integrated circuit 40, the sensor device 30 can be downsized.

Moreover, with this configuration, the electric field strength generated by the voltage signal applied to the electrode pair 36 is increased in the vicinity of the surface of the sensor device 30, thereby providing the effect of increasing dielectrophoretic force or electrophoresis force with respect to the analyte. Moreover, the electric field strength generated by the sensing electrodes 35 is increased in the vicinity of the surface of the sensor device 30, thereby providing the effect of increasing the sensitivity of the sensor device 30 to the physical property of the analyte.

In a sensor device 30 according to a fourth aspect of the present invention referring to any one of the first to third aspects, the electrode pair 36 receives a voltage signal according to the specific analyte to move the specific analyte to the arbitrary location.

With this configuration, the specific analyte can be selectively moved.

In a sensor device 30 according to a fifth aspect of the present invention referring to the fourth aspect, the electrode pair 36 receives a voltage signal according to a plurality of analytes dispersed in liquid to move a specific analyte of the plurality of analytes to the arbitrary location and to move remaining analytes away from the arbitrary location.

This configuration enables only the specific analyte to be detected even when a plurality of kinds of analytes are dispersed in liquid.

In a sensor device 30 according to a sixth aspect of the present invention referring to any one of the first to fifth aspects, a well structure 116 is formed on the electrode pair 36, and the well structure 116 has a region which a biological substance (cell 202) contained in the analyte enters.

With this configuration, the biological substance is physically adsorbed on the well structure 116, and a captured state is maintained due to interaction between the well structure 116 and the biological substance even when application of the alternating-current electric field to the electrode pair 36 is stopped after the biological substance is captured. Moreover, when the well structure 116 is introduced, it becomes possible to capture only one biological substance, and thus, it becomes possible to provide a quantitative property to the test.

A detection method according to a seventh aspect of the present invention is a detection method for detecting a third biological substance (protein 205) serving as a target of antibody-antigen reaction of a first biological substance (antibody 203) dispersed in liquid by using the sensor device 30 according to any one of the first to sixth aspects, the oscillation unit 31 including sensing electrodes 35 which are electrodes in a pair, the detection method including a step of capturing a second biological substance (cell 202) on which the first biological substance is adsorbed by the electrode pair 36, and a step of detecting a presence or absence of the third biological substance by the sensing electrodes 35.

According to the method, the second biological substance is captured at a desired location through dielectrophoresis, and the first biological substance is adsorbed on the second biological substance, which enables the first biological substance to selectively be fixed to a desired location on the sensor surface. Thus, the first biological substance is selectively fixed to only a location with high sensing sensitivity of the sensor device 30, and thereby it becomes possible to effectively increase the sensing sensitivity to the third biological substance.

In the detection method according to an eighth aspect of the present invention referring to the seventh aspect, the second biological substance is a biological substance which is activated through antigen-antibody reaction.

With this method, a range within which the permittivity changes due to the antibody-antigen reaction is drastically increased, and therefore, detection by the sensor device 30 becomes easy. That is, the sensing sensitivity of the sensor device 30 to the third biological substance is significantly increased.

A sensor unit 50 according to a ninth aspect of the present invention includes a plurality of the sensor devices 30 according to any one of the first to sixth aspects.

This configuration enables a plurality of kinds of analytes to be detected simultaneously.

A sensing method according to a tenth aspect of the present invention is a sensing method using the sensor device 30 according to any one of the first to sixth aspects, the sensing method including a moving step of moving the specific analyte dispersed in liquid to an arbitrary location by applying a voltage signal to the electrode pair 36, and a detecting step of detecting, after the moving step, the oscillation frequency of the oscillation unit 31 by the oscillation frequency detection unit 32.

This method provides an advantage similar to the advantage of the sensor device 30 according to the one aspect of the present invention.

REFERENCE SIGNS LIST 30, 30A, 30E SENSOR DEVICE
12, 32 OSCILLATION FREQUENCY DETECTION UNIT
20 TO 27 ANALYTE
31 OSCILLATION UNIT
33 RESONATOR
34 DIFFERENTIAL CIRCUIT
35 SENSING ELECTRODE
36, 36A, 36B ELECTRODE PAIR
37 CIRCUIT GROUP
40 SEMICONDUCTOR INTEGRATED CIRCUIT
50 SENSOR UNIT

The invention claimed is:

1. A sensor device for detecting a third vital substance serving as a target of antibody-antigen reaction of a first vital substance dispersed in liquid, the sensor device comprising:
   an oscillation unit formed in a semiconductor integrated circuit and having an oscillation frequency which changes in accordance with a physical property of a test object which comes into contact with the oscillation unit;
   an oscillation frequency detection unit configured to detect the oscillation frequency; and
   at least one electrode pair configured to move a specific test object dispersed in liquid to an arbitrary location,
   the oscillation unit including sensing electrodes which are electrodes in a pair,
      the electrode pair being configured to capture a second vital substance on which the first vital substance is adsorbed; and
      the sensing electrodes being configured to detect a presence or absence of the third vital substance.

2. The sensor device according to claim 1, wherein the arbitrary location to which the electrode pair moves the specific test object is an intermediate location between the pair of electrodes.

3. The sensor device according to claim 2, wherein the electrode pair and the sensing electrodes are formed in a top metal layer of the semiconductor integrated circuit.

4. The sensor device according to claim 3, wherein the electrode pair receives a voltage signal according to a plurality of test objects dispersed in liquid
   to move a specific test object of the plurality of test objects to the arbitrary location and
   to move remaining test objects away from the arbitrary location.

5. The sensor device according to claim 1, wherein a well structure is formed on the electrode pair, and the well structure has a region which a vital substance contained in the test object enters.

6. A sensor unit comprising:
   a plurality of the sensor devices each being a sensor device for detecting a third vital substance serving as a target of antibody-antigen reaction of a first vital substance dispersed in liquid,
   the sensor device including:
   an oscillation unit formed in a semiconductor integrated circuit and having an oscillation frequency which changes in accordance with a physical property of a test object which comes into contact with the oscillation unit;
   an oscillation frequency detection unit configured to detect the oscillation frequency; and
   at least one electrode pair configured to move a specific test object dispersed in liquid to an arbitrary location,
   the oscillation unit including sensing electrodes which are electrodes in a pair,
      the electrode pair being configured to capture a second vital substance on which the first vital substance is adsorbed; and
      the sensing electrodes being configured to detect a presence or absence of the third vital substance.

7. A detection method for detecting a third vital substance serving as a target of antibody-antigen reaction of a first vital substance dispersed in liquid by using a sensor device including:
   an oscillation unit formed in a semiconductor integrated circuit and having an oscillation frequency which changes in accordance with a physical property of a test object which comes into contact with the oscillation unit;
   an oscillation frequency detection unit configured to detect the oscillation frequency; and at least one electrode pair configured to move a specific test object dispersed in liquid to an arbitrary location, the oscillation unit including sensing electrodes which are electrodes in a pair, the detection method comprising:
- a step of capturing a second vital substance on which the first vital substance is adsorbed by the electrode pair, the second vital substance being a vital substance which is activated through antigen antibody reaction; and
- a step of detecting a presence or absence of the third vital substance by the sensing electrodes.

\* \* \* \* \*